(12) United States Patent
Priebe et al.

(10) Patent No.: US 6,355,784 B1
(45) Date of Patent: Mar. 12, 2002

(54) METHODS AND COMPOSITIONS FOR THE MANUFACTURE OF HALOGENATED ANTHRACYCLINES WITH INCREASED ANTITUMOR ACTIVITY, OTHER ANTHRACYCLINES, HALOGENATED SUGARS, AND GLYCOSYL DONORS

(76) Inventors: Waldemar Priebe, 4239 Emory St., Houston, TX (US) 77005; Marta Krawczyk, 175 N. Locust Hill Dr. apt. #2308, Lexington, KY (US) 40503; Piotr Skibicki, Waszyngton Street 39 Apartment 24, Warsaw 04015 (PL); Izabela Fokt; Krzysztof Dziewiszek, both of 1908 Nursery Rd., The Woodlands, TX (US) 77380; Grzegorz Grynkiewicz, µ. Zielona 16B/2, 05-092 Lomianki (PL); Roman Perez-Soler, 564 1st Ave. #20T, New York, NY (US) 10016

( * ) Notice: Subject to any disclaimer, the term of this patent is extended or adjusted under 35 U.S.C. 154(b) by 0 days.

(21) Appl. No.: 09/330,226

(22) Filed: Jun. 10, 1999

Related U.S. Application Data
(60) Provisional application No. 60/089,162, filed on Jun. 12, 1998.

(51) Int. Cl.$^7$ .............................................. C07H 15/24
(52) U.S. Cl. ..................... 536/6.4; 536/4.1; 536/17.2; 536/18.4; 536/18.7; 536/122
(58) Field of Search ................................. 536/6.4, 18.6, 536/122, 18.4, 18.7, 4.1, 17.2; 514/34

(56) References Cited

U.S. PATENT DOCUMENTS

| | | | |
|---|---|---|---|
| 4,263,428 A | | 4/1981 | Apple et al. .................. 536/6.4 |
| 4,345,070 A | | 8/1982 | Suarato et al. ................ 536/6.4 |
| 4,438,105 A | | 3/1984 | Suarato et al. ................. 514/34 |
| 4,697,005 A | * | 9/1987 | Swenton et al. ............. 536/6.4 |
| 4,772,688 A | * | 9/1988 | Horton et al. ................ 536/6.4 |

OTHER PUBLICATIONS

Bell et al., "Detection of P–glycoprotein in ovarian cancer; a molecular marker associated with multidrug resistance," *J. Clin. Oncol.*, 3(3):311–315, 1985.
Bodley et al., "DNA topoisomerase II–mediated interaction of duxorubicin and dauorubicin congeners with DNA," *Cancer Res.*, 49:5969–5978, 1989.
Booser and Hortobagyi, "Anthracycline antibiotics in cancer therapy, focus on drug resistance", *Drugs*, 47:223–258, 1994.
Capranico et al., "Sequence–selective topoisomerase II inhibition by anthracycline derivatives in SV40 DNA: Relationship with DNA binding affinity and cytotoxicity", *Biochem*, 29:562–569, 1990.

Denny et al., "Potential anti–tumor agents. 39. Anilino ring geometry of amsacrine and derivatives: relationship to DNA binding and anti–tumor activity", *J. Med. Chem.*, 26(11):1625–1630, 1983.
Bertino, "The multidrug resistance phenotype," *J. Clin. Oncol.*, 3(3):293, 1985.
Fojo et al., "Expression of a multidrug–resistnace gene in human tumors and tissues," *P.N.A.S.*, 84:265, 1987.
Ganapathi, et al., "N–Benzyladriamycin–14–valerate versus progressively doxorubicin–resistance murine tumors: cellular pharmacology and characterisation of cross–resistance in vitro and in vivo," *Br. J. Cancer*, 60:819, 1989.
Gianni et al., "New drug therapy of amyloidoses: resorption of AL–type deposits with 4'–iodo–4'–deoxydoxorubicin," *Blood*, 86(3):855–861, 1995.
Green et al., "Rapid colometric assay for cell viability: application to the quantitation of cytotoxic and growth inhibitory lymphokines," *J. Immunol. Methods*, 70:257–268, 1984.
Gros et al., "Isolation and expression of a complementary DNA that confers multidrug resistance," *Nature*, 323:728, 1986.
Israel et al., "Amelioration of adriamycin toxicity through modification of drug–DNA binding properties," *Cancer Treat Rev.* Dec;14(3–4):163–7, 1987.
Israel et al., "Comparative uptake and retention of adraimycin and N–benzyladriamycin–14–valerate in human CEM leukemic lymphocyte cell cultures," *Cancer Chemother, Pharmacol.*, 25:177, 1989.
Katsumata et al., "Prevention of breast tumor development in vivo by down–regulation of the p185$^{neu}$ Receptor", *Nature Med.*, 1(7):644–648, 1995.
Lown, "Targeting the DNA minor groove for control of biological function: progress, challenges and prospects", *Chemtracts—Org. Chem.*, 6:205–237, 1903.
Merlini et al., "Interaction of the anthracycline 4'–iodo–4'–deoxydoxorubicin with amyloid fibrils: inhibition of amyloidogenesis," *Proc. Natl. Acad. Sc. USA*, 92:2959–2963.
Norris et al., "Expression of the gene for multidrug–resistance–associated protein and outcome in patients with neuroblastoma", *N. Engl. J. Med*, 334(4):231–238, 1996.
Priebe et al., "3–'Hydroxyesorubicin: synthesis and antitumor activity," *J. Antibiot*, 43(7):838–846, 1990.

(List continued on next page.)

*Primary Examiner*—Elli Peselev
(74) *Attorney, Agent, or Firm*—Fulbright & Jaworski L.L.P.

(57) ABSTRACT

The present invention discloses new and novel halogenated anthracyclines linked through the saccharide portions. These congeners show high activity in vitro against several tumor cell lines. In doxorubicin (DOX) sensitive cell lines, they are at least as cytotoxic as DOX and in some cases more so. Many of these 4'- and 6'-fluorinated anthracyclines are more effective against multidrug-resistant tumors than was DOX, and/or have greater effectiveness than DOX against DOX sensitive cells. The compounds of this invention also have anti-amyloidogenic effects and the use of these compounds in the treatment of Alzheimer's disease is contemplated.

7 Claims, 15 Drawing Sheets

OTHER PUBLICATIONS

Priebe et al., "Removal of the basic center from doxorubicin partially overcomes multidrug resistance and decreases cardiotoxicity", *Anti–Cancer Drugs*, 4:37–48, 1993.

Priebe, "Mechanism of action–governed design of anthracycline antibiotics: a "turn–off/turn–on" approach", *Current Pharmaceutical Design*, 1:51–68, 1995.

Rubinstein et al., "Comparison of in vitro anti–cancer–drug––screening data generated with a tetrazolium assay versus a protein assay against a diverse panel of human tumor cell lines", *J. Nat'l. Cancer Inst.*, 82(13):1113–1120, 1990.

Sweatman et al., "Cytotoxicity and cellular pharmacology of N–benzyladriamycin–14–valerate in mechanistically different multidrug–resistant human leukemia cells," *J. Cell. Pharmacol.*, 1:95–102.

Traganos et al., "Effects of new N–alkyl analogues of adriamycin on in vitro survival and cell cycle progression of L1210 cells," *Cancer Res.*, 45:6273, 1985.

Wakelin, "Polyfunctional DNA incalcating agents," *Medicinal Research Rev*, 6:275–340, 1986.

\* cited by examiner

R = H; Daunorubicin
R = OH; Doxorubicin

WP563

WP715

WP722

WP745

WP600

WP743

R = H - 6′ - F - epidaunorubicin
R = OH - 6′ - F - epirubicin

A. TMSBr, CH2Cl2,
B. CH2Cl2, HgBr2, HgO mol.sieves 4A,

WP610

METHODS AND COMPOSITIONS FOR THE MANUFACTURE OF HALOGENATED ANTHRACYCLINES WITH INCREASED ANTITUMOR ACTIVITY, OTHER ANTHRACYCLINES, HALOGENATED SUGARS, AND GLYCOSYL DONORS

The present application is a continuation-in-part of co-pending U.S. patent application Ser. No. 60/089,162, filed Jun. 12, 1998. The entire text of the above-referenced disclosure is specifically incorporated by reference herein without disclaimer. The U.S. Government owns rights in the present invention pursuant to the National Institute of Health grants numbered CA 55320 and CA 50270.

BACKGROUND OF THE INVENTION

1. Field of the Invention

The present invention relates generally to the treatment of cancer. More particularly, it concerns novel compounds useful for chemotherapy, methods of synthesis of these compounds and methods of treatment employing these compounds. The novel compounds are halogenated anthracyclines related to anthracyclines such as daunorubicin and doxorubicin which are known to have antitumor activity. The use of these compounds in the treatment of Alzheimer's disease are also contemplated.

2. Description of Related Art

Resistance of tumor cells to the killing effects of chemotherapy is one of the central problems in the management of cancer. It is now apparent that at diagnosis many human tumors already contain cancer cells that are resistant to standard chemotherapeutic agents. Spontaneous mutation toward drug resistance is estimated to occur in one of selective pressure from drug therapy, although radiation therapy and chemotherapy may give rise to additional mutations and contribute to tumor progression within cancer cell populations (Goldie et al., 1979; Goldie et al., 1984; Nowell, 1986). The cancer cell burden at diagnosis is therefore of paramount importance because even tumors as small as 1 cm ($10^9$ cells) could contain as many as 100 to 1,000 drug-resistant cells prior to the start of therapy.

Selective killing of only the tumor cells sensitive to the drugs leads to an overgrowth of tumor cells that are resistant to the chemotherapy. Mechanisms of drug resistance include decreased drug accumulation (particularly in multi-drug resistance), accelerated metabolism of the drug and other alterations of drug metabolism, and an increase in the ability of the cell to repair drug-induced damage (Curt et al., 1984; and Kolate, 1986). The cells that overgrow the tumor population not only are resistant to the agents used but also tend to be resistant to other drugs, many of which have dissimilar mechanisms of action. This phenomenon, called pleiotropic drug resistance or multi-drug resistance (MDR), may account for much of the drug resistance that occurs in previously treated cancer patients. The development of drug resistance is one of the major obstacles in the management of cancer. One of the traditional ways to attempt to circumvent this problem of drug resistance has been combination chemotherapy.

Combination drug therapy is the basis for most chemotherapy employed to treat breast, lung, and ovarian cancers as well as Hodgkin's disease, non-Hodgkin's lymphomas, acute leukemias, and carcinoma of the testes. Combination chemotherapy uses the differing mechanisms of action and cytotoxic potentials of multiple drugs.

Although combination chemotherapy has been successful in many cases, the need still exists for new anti-cancer drugs. These new drugs could be such that they are useful in conjunction with standard combination chemotherapy, or these new drugs could attack drug, resistant tumors by having the ability to kill cells of multiple resistance phenotypes.

A drug that exhibits the ability to overcome multiple drug resistance could be employed as a chemotherapeutic agent either alone or in combination with other drugs. The potential advantages of using such a drug in combination with chemotherapy would be the need to employ fewer toxic compounds in the combination, cost savings, and a synergistic effect leading to a treatment regime involving fewer treatments.

The commonly used chemotherapeutic agents are classified by their mode of action, origin, or structure, although some drugs do not fit clearly into any single group. The categories include alkylating agents, anti-metabolites, antibiotics, alkaloids, and miscellaneous agents (including hormones). Agents in the different categories have different sites of action.

Antibiotics are biologic products of bacteria or fungi. They do not share a single mechanism of action. The anthracyclines daunorubicin and doxorubicin (DOX) are some of the more commonly used chemotherapeutic antibiotics. The anthracyclines achieve their cytotoxic effect by several mechanisms, including inhibition of topoisomerase II; intercalation between DNA strands, thereby interfering with DNA and RNA synthesis; production of free radicals that react with and damage intracellular proteins and nucleic acids; chelation of divalent cations; and reaction with cell membranes. The wide range of potential sites of action may account for the broad efficacy as well as the toxicity of the anthracyclines (Young et al., 1985).

The anthracycline antibiotics are produced by the fungus *Streplonlyces peuceitius* var. *caesius*. Although they differ only slightly in chemical structure, daunorubicin has been used primarily in the acute leukemias, whereas doxorubicin displays broader activity against human neoplasms, including a variety of solid tumors. The clinical value of both agents is limited by an unusual cardiomyopathy, the occurrence of which is related to the total dose of the drug; it is often irreversible. In a search for agents with high antitumor activity but reduced cardiac toxicity, anthracycline derivatives and related compounds have been prepared. Several of these have shown promise in the early stages of clinical study, and some, like epirubicin and idarubicin, are used as drugs. Epirubicin outsells doxorubucin in Europe and Japan, but it is not sold in the U.S.

The anthracycline antibiotics have tetracycline ring structures with an unusual sugar, daunosamine, attached by glycosidic linkage. Cytotoxic agents of this class all have quinone and hydroquinone moieties on adjacent rings that permit them to function as electron-accepting and donating agents. Although there are marked differences in the clinical use of daunorubicin and doxorubicin, their chemical structures differ only by a single hydroxyl group on C14. The chemical structures of daunorubicin and doxorubicin are shown in FIG. 1.

Doxorubicin's broad spectrum of activity against most hematological malignancies as well as carcinomas of the lung, breast, and ovary has made it a leading agent in the treatment of neoplastic disease (Arcamone, 1981; Lown, 1988; Priebe, 1995). Since the discovery of daunorubicin and doxorubicin (FIG. 1), the mechanistic details of the antitumor activity of anthracycline antibiotics have been actively investigated (Priebe, 1995; Priebe, 1995; Booser, 1994).

Studies have shown that the anthracycline, 4'-iodo-4'-deoxydoxorubicin (IDOX), binds strongly to amyloid fibrils. Preincubation of the amyloid enhancing factor with IDOX significantly reduces formation of amyloid deposits (Merlini et al., 1995). Amyloid fibril formation is involved in a number of diseases, including amyloidosis, prion diseases and Alzheimer's disease. Amyloidosis is a rapidly progressive disease, characterized by the tissue deposition of paraproteins as insoluble fibrils, leading to organ dysfunction and death. Patients with amyloidosis, showed substantial clinical improvement, as a result of amyloid resorption, when treated with IDOX (Gianni et al., 1995). Prion diseases are characterized by the accumulation of protease-resistant insoluble forms of the prion-protein into aggregates of amyloid fibrils in the brain. In tests on an experimental Syrian-hamster model of prion disease, IDOX treated hamsters had a delayed onset of the disease and their survival time was prolonged. Neuropathologial examination of the treated hamster brains showed a parallel delay in the accumulation of amyloid fibrils with respect to the untreated controls (Tagliavini et al., 1997).

Unfortunately, concomitant with its antitumor and anti-amyloidogenic activities, DOX can produce adverse systemic effects, including acute myelosuppression, cumulative cardiotoxicity, and gastrointestinal toxicity (Young et al., 1985). At the cellular level, in both cultured mammalian cells and primary tumor cells, DOX can select for multiple mechanisms of drug resistance that decrease its chemotherapeutic efficacy. These mechanisms include P-gp-mediated MDR, characterized by the energy-dependent transport of drugs from the cell (Bradley et al., 1988), and resistance conferred by decreased topoisomerase II activity, resulting in the decreased anthracycline-induced DNA strand scission (Danks et al., 1987; Pommier et al., 1986; Moscow et al., 1988.

Among the potential avenues of circumvention of systemic toxicity and cellular drug resistance of the natural anthracyclines is the development of semi-synthetic anthracycline analogues which demonstrate greater tumor-specific toxicity and less susceptibility to various forms of resistance.

SUMMARY OF THE INVENTION

The present invention seeks to overcome drawbacks inherent in the prior art by providing compositions of agents that display increased cytotoxicity when compared with doxorubicin and can prevent and/or overcome multi-drug resistance. This invention involves novel compounds that have utility as antitumor and/or chemotherapeutic drugs, methods of synthesizing these compounds and methods of using these compounds to treat patients with cancer. The invention is generally based on the discovery that anthracycline derivatives that have fluorine groups attached to their sugar moiety have a surprisingly strong ability to kill tumor cells.

The inventors have designed halogenated anthracyclines, as exemplified by fluorinated anthracyclines, connected at positions which would not interfere with DNA binding, and the inventors have synthesized anthracyclines having sugar portions that have been halogenated at positions 4' and 6'. These actions produced halogenated anthracyclines which exhibit activity substantially different from the activities of doxorubicin or daunorubicin. These compounds are active against doxorubicin resistant tumors and/or are more cytotoxic than doxorubicin against sensitive tumors. This indicates that halogenated anthracyclines are mechanistically different from doxorubicin and daunorubicin.

In some specific embodiments, the anthracycline compounds of the present invention have the general formula:

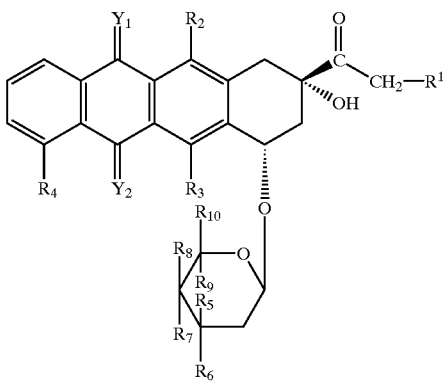

wherein: $R^1$ is a hydrogen (—H) group, a hydroxyl group (—OH), a methoxy group (—OCH$_3$), an aryl group having 1–20 carbon atoms, a fatty acyl group having the general structure —O—CO(CH$_2$)$_n$CH$_3$, wherein n=an integer from 1 to about 20, or a fatty acyl group having the general structure —O—CO(CH$_2$)$_l$(CH=CH)$_m$(CH$_2$)$_n$CH$_3$, wherein l is an integer between 1 to 3, m is an integer between 1 and about 6, and n is an integer between 1 to about 9; each of $R^2$ and $R^3$ is, independently of the other, a hydrogen (—H) group, a hydroxyl group (—OH), a methoxy group (—OCH$_3$) or a double bonded oxygen moiety; $R^4$ is a hydrogen (—H) group, a hydroxyl group (—OH), a methoxy group (—OCH$_3$) or a halide; each of $Y^1$ and $y^2$ is, independently of the other, a hydrogen (—H) group; a hydroxyl group (—OH); a methoxy group (—OCH$_3$); or a double bonded oxygen, sulphur, or nitrogen group; $R^5$ is —H, —OH, —OR$^{11}$, —SH, —SR$^{11}$, —NH$_2$, or —NHR$^{11}$; $R^6$ is —H, —OH, —OR$^{11}$, —SH, —SR$^{11}$, —NR$^{11}$$_2$, —NR$^{11}$$_2$, or —NHR$^{11}$; $R^7$ is —H, —OH, —OR$^{11}$, —SH, —SR$^{11}$, —NH$_2$, —NHR$^{11}$, F, I, Br, or Cl, with the proviso that $R^7$ can be I only when $R^6$ is —OH or —SH; $R^8$ is —H, —OH, —OR$^{11}$, —SH, —SR$^{11}$, —NH$_2$, —NHR$^{11}$, F, I, Br, or Cl; $R^9$ is CH$_3$, CH$_2$F, CH$_2$I, CH$_2$Br, or CH$_2$Cl; $R^{10}$ is H, F, I, Br, or Cl; and $R^{11}$ is a hydrogen (—H) group, a hydroxyl group (—OH), a methoxy group (—OCH$_3$), an aryl group having 1–20 carbon atoms, a fatty acyl group having the general structure —O—CO(CH$_2$)$_n$CH$_3$, wherein n=an integer from 1 to about 20, or a fatty acyl group having the general structure —O—CO(CH$_2$)$_l$(CH=CH)$_m$(CH$_2$)$_n$CH$_3$, wherein l is an integer between 1 to 3, m is an integer between 1 and about 6, and n is an integer between 1 to about 9.

Certain specific embodiments of the anthracyclines of the invention are:

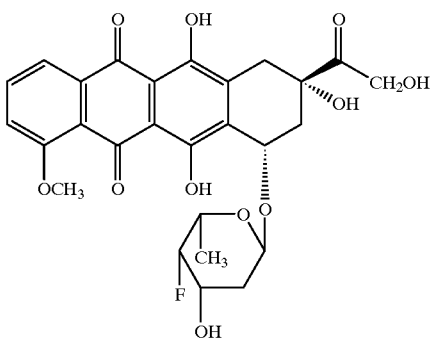

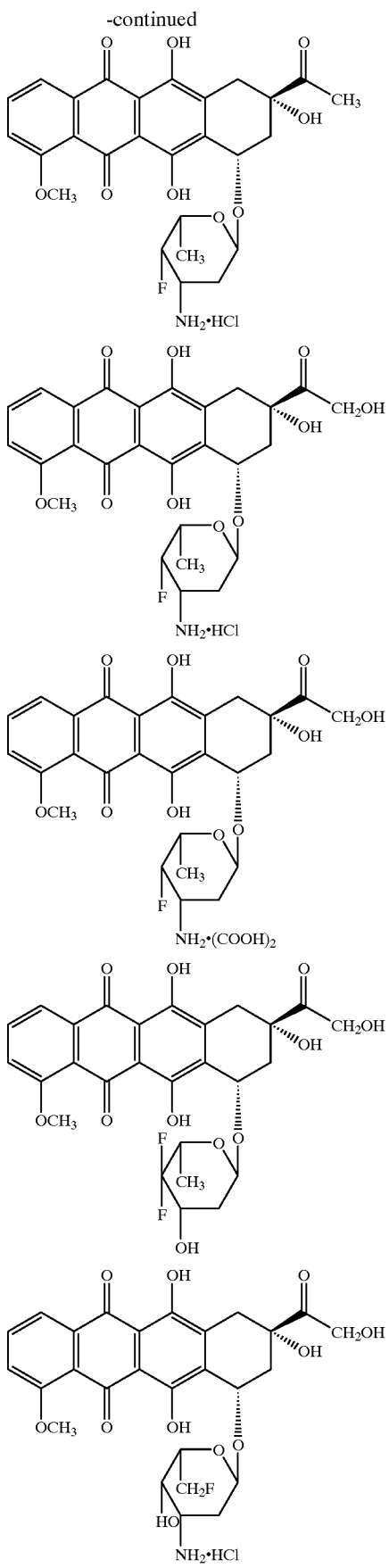

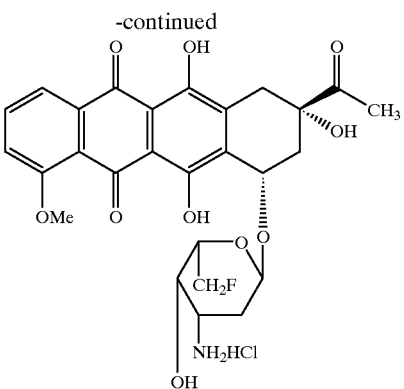

Specific embodiments of the anthracylines of the invention may have the structures shown in FIG. 4, FIG. 5, FIG. 6, FIG. 7, FIG. 9, FIG. 11, FIG. 14, or FIG. 19.

The present application also comprises methods of preparing anthracyclines. In general, the methods comprise a step of preparing or obtaining an anthracycline of formula:

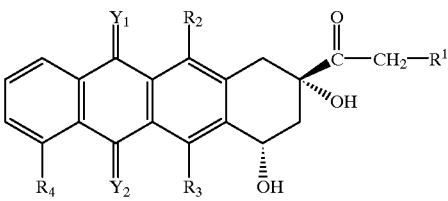

wherein: $R^1$ is a hydrogen (—H) group, a hydroxyl group (—OH), a methoxy group (—OCH$_3$), an aryl group having 1–20 carbon atoms, a fatty acyl group having the general structure —O—CO(CH$_2$)$_n$CH$_3$, wherein n=an integer from 1 to about 20, or a fatty acyl group having the general structure —O—CO(CH$_2$)$_l$(CH=CH)$_m$(CH$_2$)$_n$CH$_3$, wherein l is an integer between 1 to 3, m is an integer between 1 and about 6, and n is an integer between 1 to about 9; each of $R^2$ and $R^3$ is, independently of the other, a hydrogen (—H) group, a hydroxyl group (—OH), a methoxy group (—OCH$_3$) or a double bonded oxygen moiety; $R^4$ is a hydrogen (—H) group, a hydroxyl group (—OH), a methoxy group (—OCH$_3$) or a halide; each of $Y^1$ and $y^2$ is, independently of the other, a hydrogen (—H) group; a hydroxyl group (—OH); a methoxy group (—OCH$_3$); or a double bonded oxygen, sulphur, or nitrogen group. The methods further comprise a step of obtaining or preparing a saccharide of general formula:

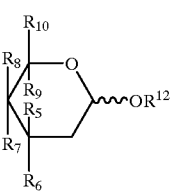

wherein: $R^5$ is —H, —OH, —OR$^{11}$, —SH, —SR$^{11}$, —NH$_2$, or —NHR$^{11}$ or N$_3$; $R^6$ is —H, —OH, —OR$^{11}$, —SH, —SR$^{11}$, —NH$_2$, NR$^{11}_2$, or —NHR$^{11}$ or N$_3$; $R^7$ is —H, —OH, —OR$^{11}$, —SH, —SR$^{11}$, —NH$_2$, —NHR$^{11}$, N$_3$, F, I, Br, or Cl, with the proviso that $R^7$ can be I only when $R^6$ is —OH or —SH; $R^8$ is —H, —OH, —OR$^{11}$, —SH, —SR$^{11}$, —NH$_2$, —NHR$^{11}$, N$_3$, F, I, Br, or Cl; $R^9$ is CH$_3$ CH$_2$F, CH$_2$I, CH$_2$Br, or CH$_2$Cl; $R^{10}$ is H, F, I, Br, or Cl; $R^{11}$ is a hydrogen (—H) group, a hydroxyl group (—OH), a methoxy group (—OCH$_3$), an aryl group having 1–20 carbon atoms, a fatty acyl group having the general structure —O—CO(CH$_2$)$_n$CH$_3$, wherein n=an integer from 1 to about 20, or a fatty acyl group having the general structure —O—CO(CH$_2$)$_l$(CH=CH)$_m$(CH$_2$)$_n$CH$_3$, wherein l is an integer between 1 to 3, m is an integer between 1 and about 6, and n is an integer between 1 to about 9; and R$^{12}$ is an alkyl group, an S-alkyl group, an acyl group, an S-acyl group, a silylalkyl group, a halide, or any other leaving group. The anthracycline is then conjugated to the saccharide under suitable conditions to produce a glycosidic bond and result in a compound of the formula:

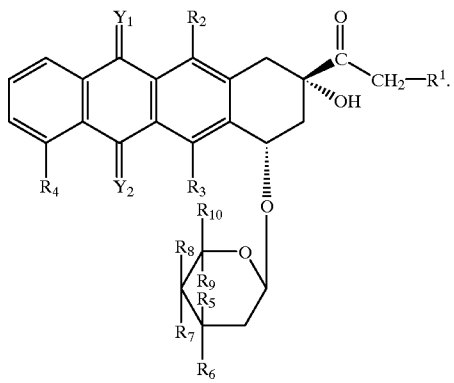

In some preferred embodiments, the method of anthracycline synthesis comprises steps of synthesizing a 4 or 6 halogen-substituted sugar moiety; conjugating said sugar moiety to a doxorubicin or daunorubicin analog via a glycosidic bond; removing extraneous solvent to obtain a crude halogenated anthracycline; and purifying the crude halogenated anthracycline.

The invention encompasses novel methods of chemical synthesis wherein a glycosyl donor saccharide having a 3' or 4' amine group masked as an azide is employed. In a specific example of such a synthesis, one may couple an anthracycline to a saccharide by obtaining an anthracycline, obtaining a saccharide which has a 3' or 4' amine group masked as an azide group, conjugating the anthracycline to the saccharide via a glycosidic bond, and reducing the azide to an amine to obtain a 3'- or 4'-amine anthracycline. In some preferred embodiments, the amine group is placed at the 3' position on the saccharide. Some preferred saccharides for the practice of this method are halogenated sugars comprising the structure:

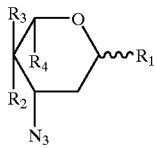

wherein: R$^1$ is any suitable leaving group that will allow for formation of a glycosidic bond; R$^2$, R$^3$, and R$^4$ are: H, OH, OR$^5$, SH, SR$^5$, NHR$^5$, NH$_2$, NR$^5{}_2$, F, I, Br, Cl, and R$^5$ is: a hydrogen (—H) group, a hydroxyl group (—OH), a methoxy group (—OCH$_3$), an aryl group having 1–20 carbon atoms, a fatty acyl group having the general structure —O—CO(CH$_2$)$_n$CH$_3$, wherein n=an integer from 1 to about 20, or a fatty acyl group having the general structure —O—CO(CH$_2$)$_l$(CH=CH)$_m$(CH$_2$)$_n$CH$_3$, wherein l is an integer between 1 and about 6, and n is an integer between 1 to about 9.

In a more general aspect, the invention comprises glycosyl donors having a structure:

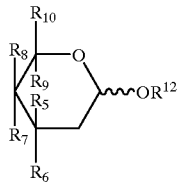

wherein: R$^5$ is —H, —OH, —OR$^{11}$, —SH, —SR$^{11}$, —NH$_2$, or —NHR$^{11}$; R$^6$ is —H, —OH, —OR$^{11}$, —SH, —SR$^{11}$, —NH$_2$, NR$^{11}{}_2$, or —NHR$^{11}$; R$^7$ is —H, —OH, —OR$^{11}$, —SH, —SR$^{11}$, —NH$_2$, —NHR$^{11}$, F, I, Br, or Cl, with the proviso that R$^7$ can be I only when R$^6$ is —OH or —SH; R$^8$ is —H, —OH, —OR$^{11}$, —SH, —SR$^{11}$, —NH$_2$, —NHR$^{11}$, F, I, Br, or Cl; R$^9$ is CH$_3$, CH$_2$F, CH$_2$I, CH$_2$Br, or CH$_2$Cl; R$^{10}$ is 14, F, I, Br, or Cl; R$^{11}$ is a hydrogen (—H) group, a hydroxyl group (—OH), a methoxy group (—OCH$_3$), an aryl group having 1–20 carbon atoms, a fatty acyl group having the general structure —O—CO(CH$_2$)$_n$CH$_3$, wherein n=an integer from 1 to about 20, or a fatty acyl group having the general structure —O—CO(CH$_2$)$_l$(CH=CH)$_m$(CH$_2$)$_n$CH$_3$, wherein l is an integer between 1 to 3, m is an integer between 1 and about 6, and n is an integer between 1 to about 9; and R$^{12}$ is an alkyl group, an S-alkyl group, an acyl group, an S-acyl group, a silylalkyl group, a halide, or any other leaving group.

The above-described method of forming a compound comprising a glycosyl donor conjugated to an aglycon through a glycosyl bond comprising obtaining a glycosyl donor having a structure:

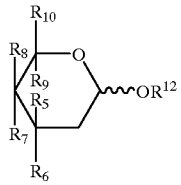

wherein: R$^5$ is —H, —OH, —OR$^{11}$, —SH, —SR$^{11}$, —NH$_2$, or —NHR$^{11}$; R$^6$ is —H, —OH, —OR$^{11}$, —SH, —SR$^{11}$, —NH$_2$, NR$^{11}{}_2$, or —NHR$^{11}$; R$^7$ is —H, —OH, —OR$^{11}$, —SH, —SR$^{11}$, —NH$_2$, —NHR$^{11}$, F, I, Br, or Cl, with the proviso that R$^7$ can be I only when R$^6$ is —OH or —SH; R$^8$ is —H, —OH, —OR$^{11}$, —SH, —SR$^{11}$, —NH$_2$, —NHR$^{11}$, F, I, Br, or Cl; R$^9$ is CH$_3$, CH$_2$F, CH$_2$I, CH$_2$Br, or CH$_2$Cl; R$^{10}$ is H, F, I, Br, or Cl; R$^{11}$ is a hydrogen (—H) group, a hydroxyl group (—OH), a methoxy group (—OCH$_3$), an aryl group having 1–20 carbon atoms, a fatty acyl group having the general structure —O—CO(CH$_2$)$_n$CH$_3$, wherein n=an integer from 1 to about 20, or a fatty acyl group having the general structure —O—CO(CH$_2$)$_l$(CH=CH)$_m$(CH$_2$)$_n$CH$_3$, wherein l is an integer between 1 to 3, m is an integer between 1 and about 6, and n is an integer between 1 to about 9; and R$^{12}$ is an alkyl group, an S-alkyl group, an acyl group, an S-acyl group, a silylalkyl group, a halide, or any other leaving group; obtaining an aglycon; and forming a glycosidic bond between the glycosyl donor and the aglycon. The aglycon can be any form of biological molecule.

The present invention also comprises halogenated sugars that are useful for a variety of drug and chemical synthesis purposes. Preferably, these sugars are halogenated at the 4' or the 6' position. Generally, exemplary halogenated sugars may comprise the structure:

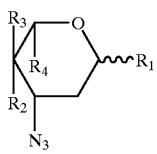

wherein: $R^1$ is any suitable leaving group that will allow for formation of a glycosidic bond; $R^2$, $R^3$, and $R^4$ are: H, OH, $OR^5$, SH, $SR^5$, $NHR^5$, $NH_2$, $NR^5{}_2$, F, I, Br, Cl, or a sugar; and $R^5$ is: a hydrogen (—H) group, a hydroxyl group (—OH), a methoxy group (—$OCH_3$), an aryl group having 1–20 carbon atoms, a fatty acyl group having the general structure —O—$CO(CH_2)_nCH_3$, wherein n=an integer from 1 to about 20, or a fatty acyl group having the general structure —O—$CO(CH_2)_l(CH=CH)_m(CH_2)_nCH_3$, wherein l is an integer between 1 to 3, m is an integer between 1 and about 6, and n is an integer between 1 to about 9.

Several specific exemplary halogenated sugars are shown in FIG. 17.

The invention also relates to methods of obtaining derivatives of DOX by the use of azides as blocking groups and linking an anthracycline to a saccharide. The steps required include obtaining an anthracycline; obtaining a saccharide which is masked by an azide group; conjugating the anthracycline to the saccharide via a glycosidic bond; and reducing the azide to an amine to obtain an amine anthracycline.

Another important embodiment of this invention is a method for treating Alzheimer's disease comprising obtaining an anthracycline compound as described above, and administering to a person that either has Alzheimer's disease or has the predisposition for Alzheimer's disease, a pharmaceutically acceptable formulation of the anthracycline compound in a dose effective for the treatment of Alzheimer's disease. The treatment results in curing, improving, or preventing Alzheimer's disease in a person. In another aspect the invention comprises obtaining the compound described above and administering the compound, in addition to another anti-Alzheimer's drug, to a person having or at the risk of developing Alzheimer's disease in an amount effective to cure, improve, and/or prevent Alzheimer's disease.

In devising the synthetic schemes and compounds of the present invention, the inventors have created a variety of novel compounds. These compounds are described elsewhere in the specification and figures, and are given "WP" numbers. The structure of a compound designated with a "WP" number is ascertainable by reviewing the specification and figures. Exemplary specific compounds that are encompassed by the invention are WP351, WP556, WP557, WP559, WP564, WP563, WP715, WP722, WP745, WP587, WP588, WP589, WP590, WP592, WP600, WP610, WP743, WP458, WP508, and WP526. Also encompassed by the invention are 6'-F-epidaunorubicin and 6'-F-epirubicin.

The invention also considers methods of treating a patient with cancer, comprising administering to the patient a therapeutically effective amount of the contemplated halogenated anthracycline compounds and therapeutic kits comprising, in suitable container means, a pharmaceutically acceptable composition comprising the contemplated halogenated anthracycline compounds.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The present invention provides new and novel DNA intercalating agents. These agents are anthracyclines halogenated at the C-4' or C-6' in the sugar portions. These compounds show high activity against resistant tumors and cells. A novel approach of the invention produces compounds that are as active or more so than the parent compounds. Furthermore, the inventors' discovery is also for the design of effective DNA-binding halogenated anthracyclines.

Figure 1:
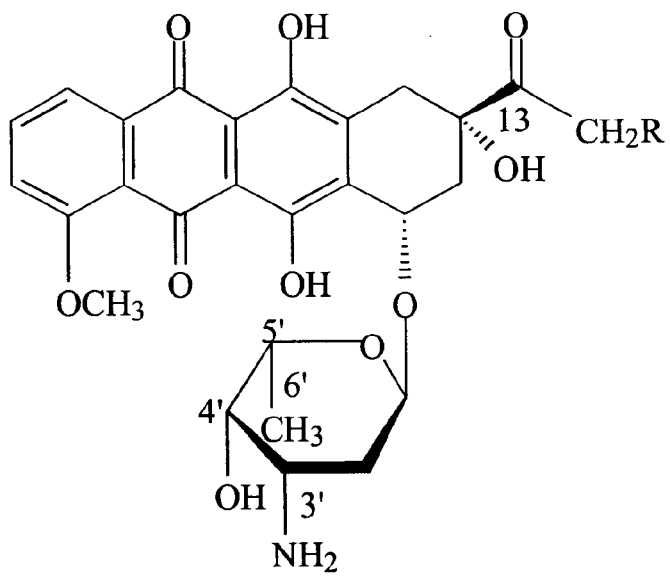
FIG. 1. Structures of daunorubicin and doxorubicin.

The anthracycline compounds have a tetracycline ring structure with sugars attached by a glycosidic linkage. Cytotoxic agents of this class have quinone and hydroquinone moieties that permit them to function as electron-accepting and electron donating agents. Doxorubicin and daunorubicin are examples of compounds of this class (FIG. 1). These compounds act by intercalating with DNA. Examples of exemplary anthracyclinones and anthracyclines are given in Table 1.

TABLE 1

List of Exemplary anthracyclinones and anthracyclines.

Anthracyclinones

Rhodomycinone
Isorhodomycinone
Pyrromycinone
4-Demethoxydaunomycinone
4-Demethoxyadriamycinone

TABLE 1-continued

List of Exemplary anthracyclinones and anthracyclines.

Daunomycinone
Adriamycinone

Anthracyclines

Figure 15:
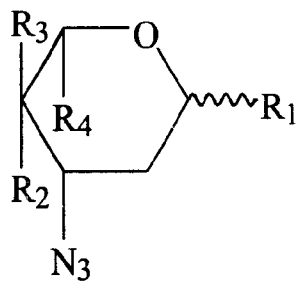
FIG. 15 General structure of exemplary glycosyl donors.

Daunorubicin
Doxorubicin
Pyrromycin
Isorhodomycine
Carminomycine
Doxorubicine 14-esters:       Doxorubicin 14-acetate
                              Doxorubicin 14-propionate
                              Doxorubicin 14-octanoate
                              Doxorubicine 14-benzoate
                              Doxorubicine 14-phenylacetate
4'-Epidaunorubicin
4'-Epidoxorubicin
4'-Iododaunorubicin
4'-Iododoxorubicin
4'-Deoxydaunorubicin
4'-Deoxydoxorubicin
3'-Hydroxydaunorubicine
3'-Hydroxydoxorubicin
4-Demethoxydaunorubicin
4-Demethoxydoxorubicin
4'-Epi-4-demethoxydaunorubicin
4'-Epi-4-demethoxydoxorubicin FIG. 15 contains an exemplary general formula for the glycosyl donor sugars that can be conjugated to anthracyclines. In FIG. 15, $R^1$ is any suitable leaving group that will allow for formation of a glycosidic bond, and $R^2$, $R^3$, and $R^4$ are any group that is suitable for synthesis of anthracyclines. In particular $R^2$, $R^3$, and $R^4$ may be, as suitable: H, OH, —$OR^5$, SH, $SR^5$, $NHR^5$, $NH_2$, $NR^5{}_2$, F, I, Br, Cl, or a sugar. $R^5$ may be, as suitable: a hydrogen (—H) group, a hydroxyl group (—OH), a methoxy group (—$OCH_3$), an aryl group having 1–20 carbon atoms, a fatty acyl group having the general structure —O—CO($CH_2$)$_n$$CH_3$, wherein n=an integer from 1 to about 20, or a fatty acyl group having the general structure —O—CO($CH_2$)$_l$(CH=CH)$_m$($CH_2$)$_n$$CH_3$, wherein l is an integer between 1 to 3, m is an integer between 1 and about 6, and n is an integer between 1 to about 9.

Figure 16:
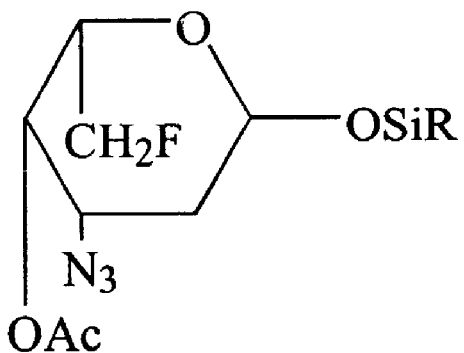
FIG. 16 Specific structures of exemplary glycosyl donors.
Figure 16:
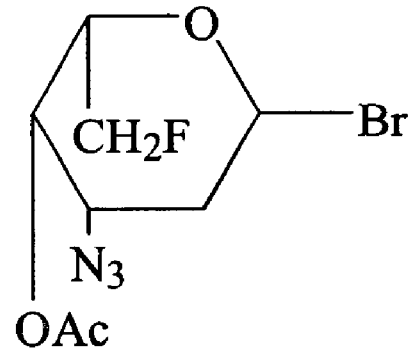
Figure 16:
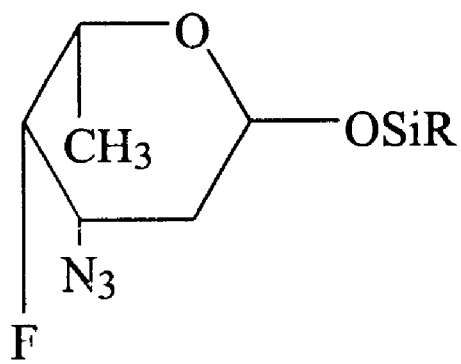
Figure 16:
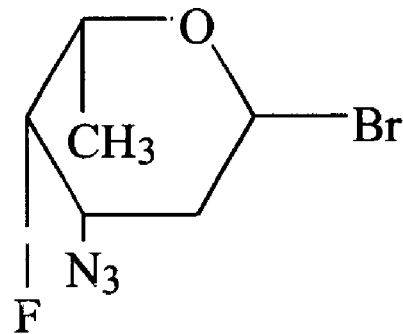
Figure 16:
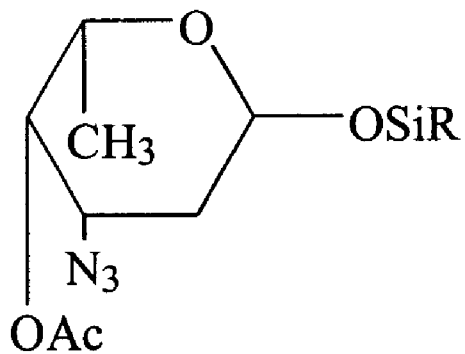
Figure 16:
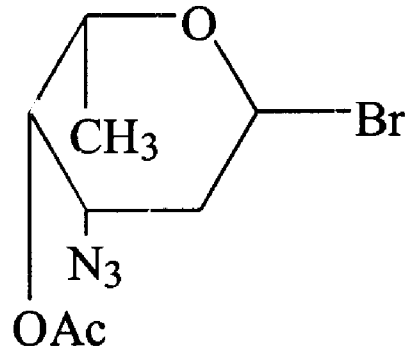
Figure 17:
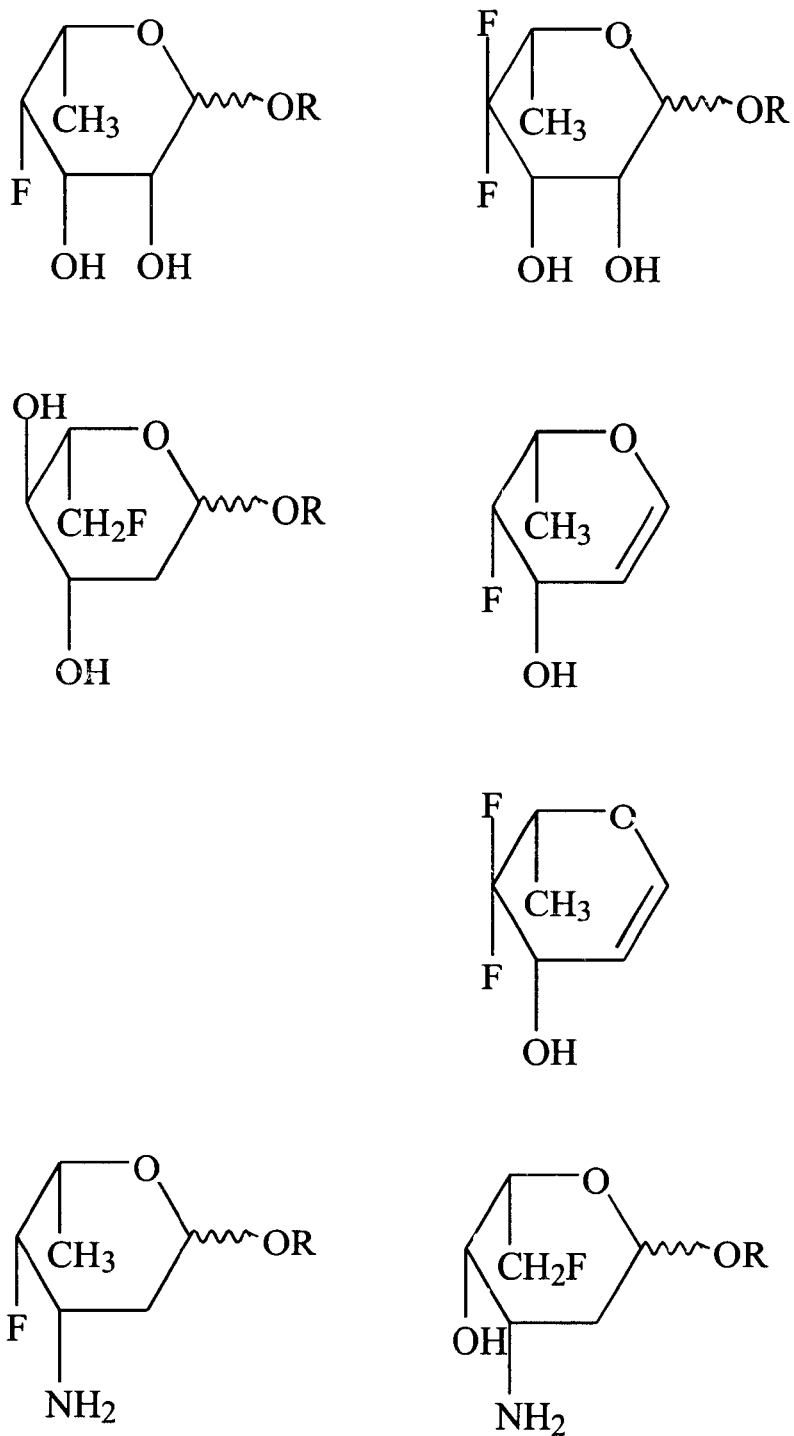
FIG. 17 Exemplary structures of halogenated sugars.

Exemplary specific structures of the general formula of FIG. 15 are found in FIG. 16. The glycosyl donors of FIG. 15 and FIG. 16 may be coupled with any anthracycline or other aglycon via a glycosidic bond. In this regard, the invention is not limited to the synthesis of anthracyclines but rather encompasses such donors coupled with any biologically relevant aglycon.

HALOGENATED ANTHRACYCLINES

Figure 2:
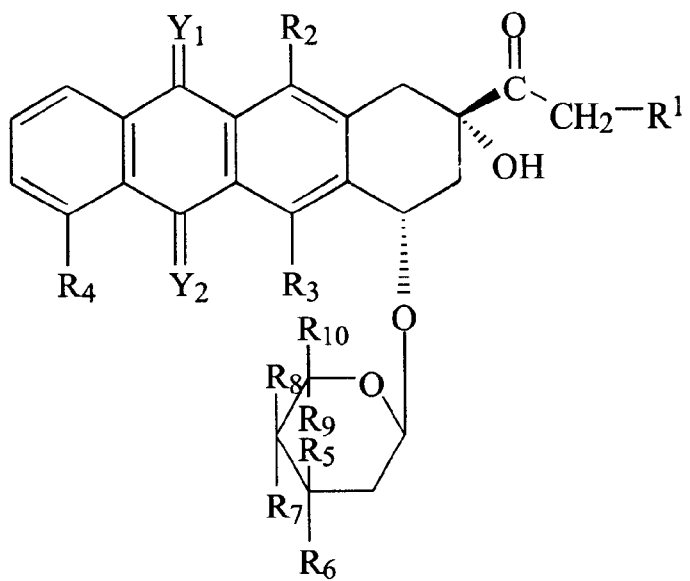
FIG. 2. Structure of exemplary fluoro anthracyclines.

The generic formula for the compounds of this invention is given in FIG. 2. In FIG. 2: $R^1$ is a hydrogen (—H) group, a hydroxyl group (—OH), a methoxy group (—$OCH_3$), an aryl group having 1–20 carbon atoms, a fatty acyl group having the general structure —O—CO($CH_2$)$_n$$CH_3$, wherein n=an integer from 1 to about 20, or a fatty acyl group having the general structure —O—CO($CH_2$)$_l$(CH=CH)$_m$($CH_2$)$_n$$CH_3$, wherein l is an integer between 1 to 3, m is an integer between 1 and about 6, and n is an integer between 1 to about 9; each of $R^2$ and $R^3$ is, independently of the other, a hydrogen (—H) group, a hydroxyl group (—OH), a methoxy group (—$OCH_3$) or a double bonded oxygen moiety; $R^4$ is a hydrogen (—H) group, a hydroxyl group (—OH), a methoxy group (—$OCH_3$) or a halide; each of $Y^1$ and $y^2$ is, independently of the other, a hydrogen (—H) group; a hydroxyl group (—OH); a methoxy group (—$OCH_3$); or a double bonded oxygen, sulphur, or nitrogen group; $R^5$ is —H, —OH, —$OR^{11}$, —SH, —$SR^{11}$, —$NH_2$, or —$NHR^{11}$; $R^6$ is —H, —OH, —$OR^{11}$, —SH, —$SR^{11}$, —$NH_2$, —$NR^{11}{}_2$, or —$NHR^{11}$; $R^7$ is —H, —OH, —$OR^{11}$, —SH, —$SR^{11}$, —$NH_2$, —$NHR^{11}$, F, I, Br, or Cl, with the proviso that $R^7$ can be I only when $R^6$ is —OH or —SH; $R^1$ is —H, —OH, —$OR^{11}$, —SH, —$SR^{11}$, —$NH_2$, —$NHR^{11}$, F, I, Br, or Cl; $R^9$ is $CH_3$, $CH_2F$, $CH_2I$, $CH_2Br$, or $CH_2Cl$; $R^{10}$ is H, F, I, Br, or Cl; and $R^{11}$ is a hydrogen (—H) group, a hydroxyl group (—OH), a methoxy group (—$OCH_3$), an aryl group having 1–20 carbon atoms, a fatty acyl group having the general structure —O—CO($CH_2$)$_n$$CH_3$, wherein n=an integer from 1 to about 20, or a fatty acyl group having the general structure —O—CO($CH_2$)$_l$(CH=CH)$_m$($CH_2$)$_n$$CH_3$, wherein l is an integer between 1 to 3, m is an integer between 1 and about 6, and n is an integer between 1 to about 9.

Following long-standing patent law convention, the words "a" and "an", when used in the specification including the claims, denotes one or more.

The symbol "∼∼∼" when used in the specification or the FIGs. denotes that the group attached to that symbol may assume more than one position. The phrase "AcO" in the specification and FIGs. denotes an acetyl blocking group ($CH_3CO$).

"Aryl" may be a phenyl group, unsubstituted or substituted with a nitro, carboxy, sulfonic acid, hydroxy, oxyalkyl, or halide.

The term "saccharide" includes oxidized, reduced or substituted saccharides. Saccharides of this invention include, but are not limited to, ribose, arabinose, xylose, lyxose, allose, altrose, glucose, mannose, fructose, gulose, idose, galactose, talose, ribulose, sorbose, tagatose, gluconic acid, glucuronic acid, glucaric acididuronic acid rhamnose, fucose, N-acetyl glucosamine, N-acetyl galactosamine, N-acetyl neuraminic acid, sialic acid, derivatives of saccharides such as acetals, amines, and phosphorylated sugars, oligosaccharides, as well as open chain forms of various sugars, and the like.

Figure 9:
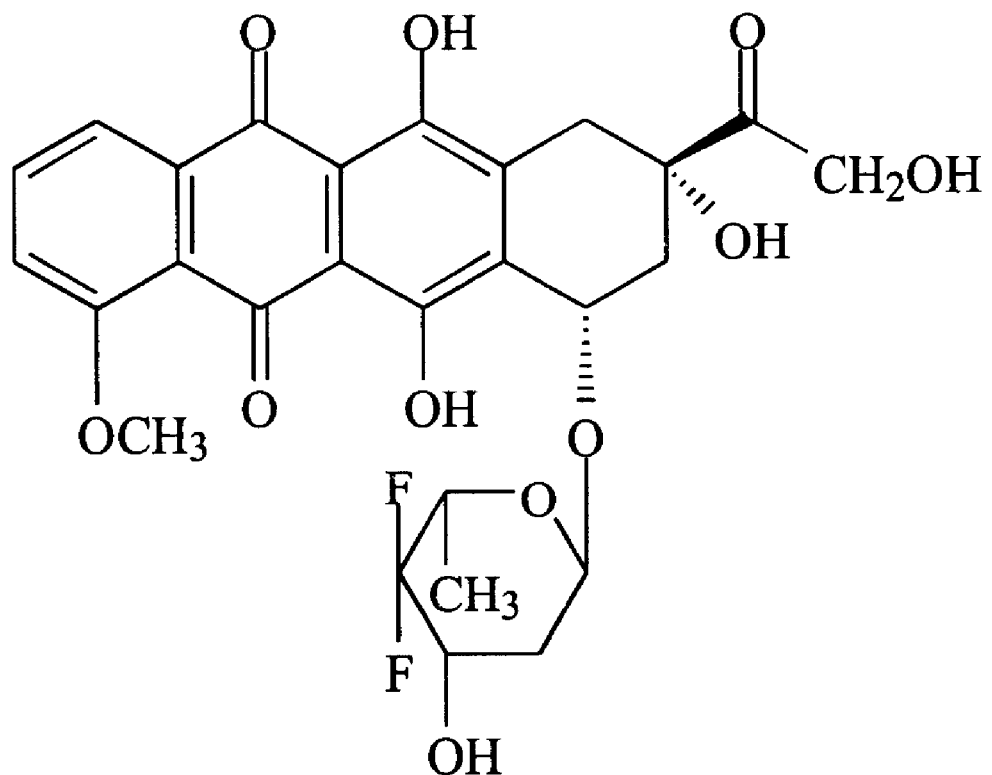
FIG. 9. Structure of 3'-deamino-4'-deoxy-4',4'-difluoro-3'-hydroxy-doxorubicin (WP 600).
Figure 11:
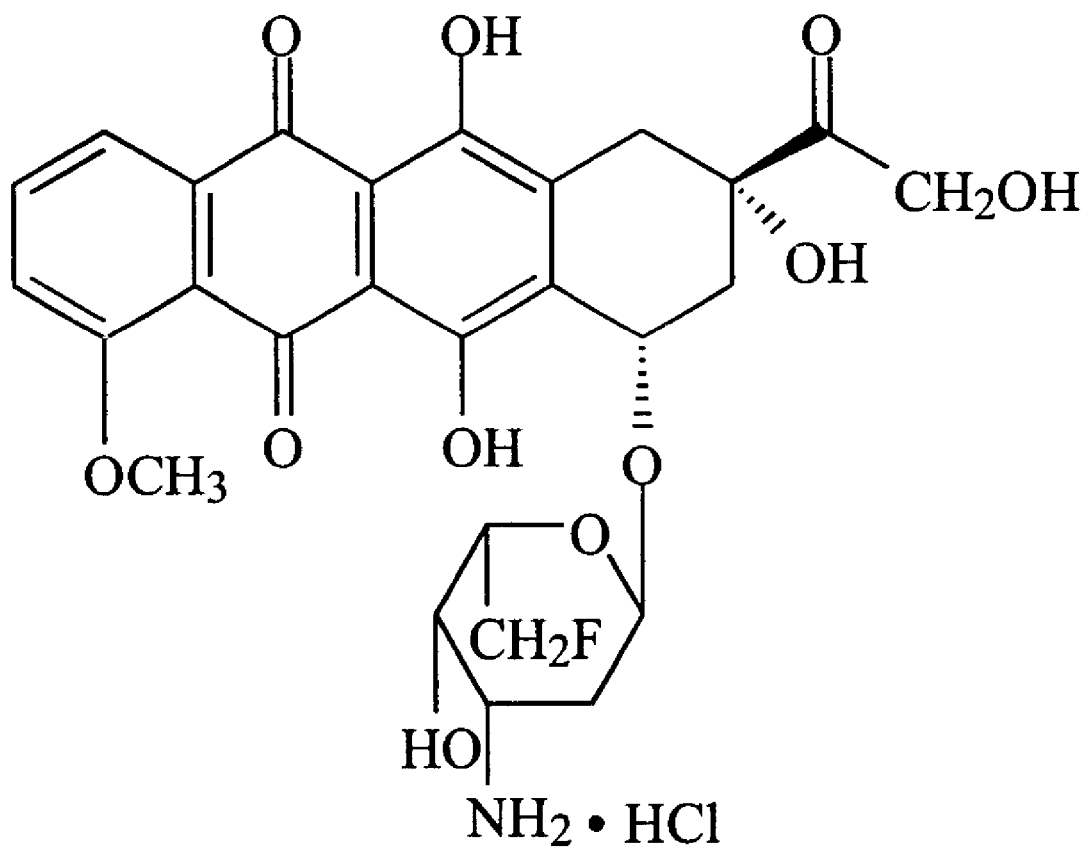
FIG. 11. Structure of 6'-fluoro-doxorubicin (WP 743).
Figure 14:
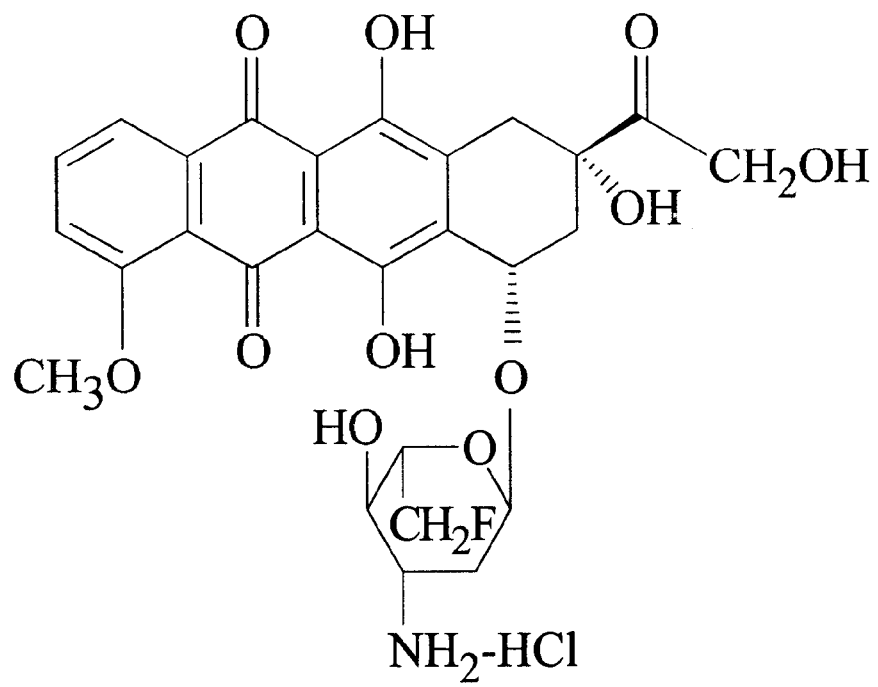
FIG. 14 Structures of 6'-F-epidaunorubicin and 6'-F-epirubicin.
Figure 19:
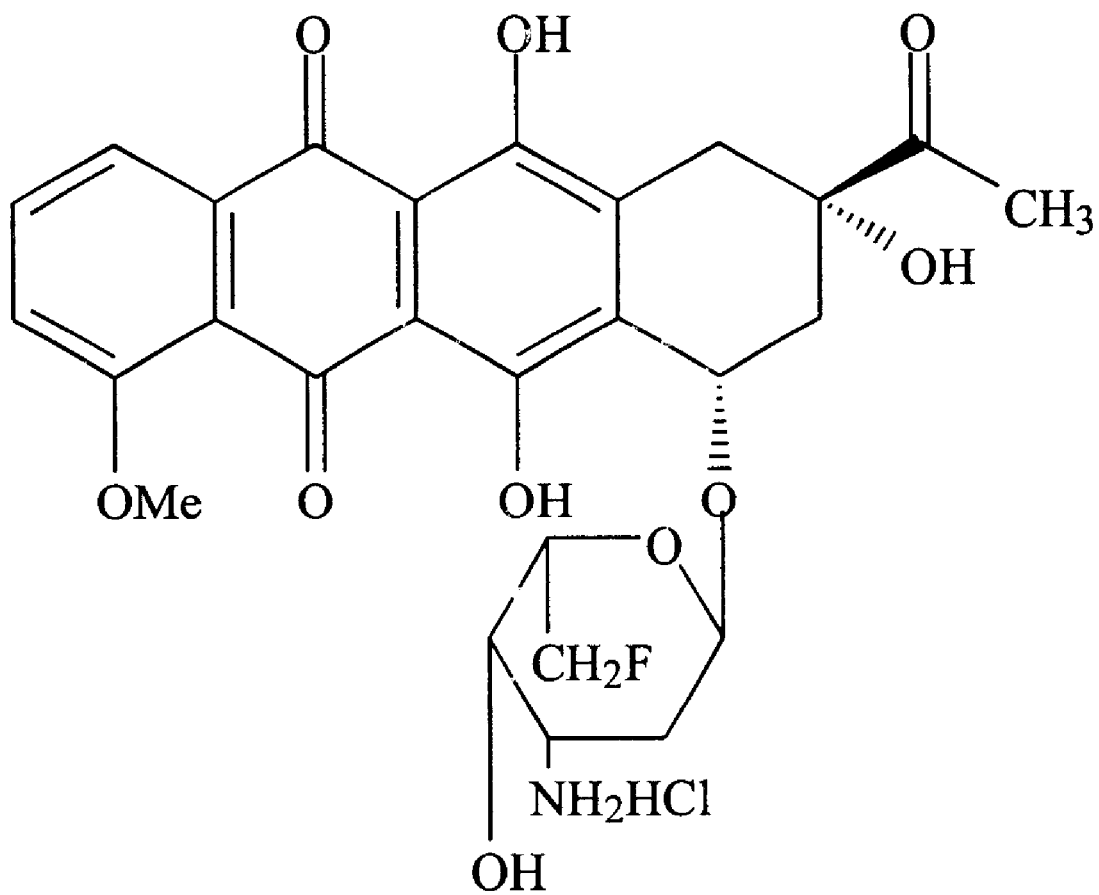
FIG. 19 Structure of WP 610.

An individual skilled in the art of organic synthesis in light of the present disclosure is able to prepare a large variety of halogenated sugars and halogenated anthracyclines which are expected to have chemotherapeutic activities and may be used in the treatment of cancer and/or other diseases. Exemplary halogenated anthracyclines of the present invention are WP 563 (FIG. 4), WP 715 (FIG. 5), WP 722 (FIG. 6), WP 745 (FIG. 7), WP 600 (FIG. 9), WP 743 (FIG. 11), 6'-F-epidaunorubicin (FIG. 14), 6'-F-epirubicin (FIG. 14), and WP 610 (FIG. 19). Most of these specific halogenated anthracyclines have been synthesized by the inventors and have been analyzed and the structure confirmed by NMR and elemental analysis. The methods of the present application enable one of skill in the art to synthesize these compounds and many other related compounds without undue experimentation.

The present discoveries may be utilized in conjunction with certain techniques that are well-known in the biological arts and that are further described in the following sections.

PHARMACEUTICAL COMPOSITIONS

The anti-tumor compounds of this invention can be administered to kill tumor cells by any method that allows contact of the active ingredient with the agent's site of action in the tumor. They can be administered by any conventional methods a vailable for use in conjunction with pharmaceuticals, either as individual therapeutically active ingredients or in a combination of therapeutically active ingredients. They can be administered alone but are generally administered with a pharmaceutically acceptable carrier selected on the basis of the chosen route of administration and standard pharmaceutical practice.

Aqueous compositions of the present invention will have an effective amount of anthracycline to kill or slow the growth of cancer cells. Further the potential recognition of genes can be accomplished by the synthesis of halogenated anthracyclines with specific structures that allow for the recognition of specific parts of DNA. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

A. Parenteral Administration

The active compounds will often be formulated for parenteral administration, e.g., formulated for injection via the intravenous, intramuscular, subcutaneous, or even intraperitoneal routes. The preparation of an aqueous composition that contains an anthracycline of the present invention as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some forms, it will be desirable to formulate the novel compounds in salt form, generally to improve the solubility and bioavailability and to provide an active drug form more readily assimilated. As used herein, the term "pharmaceutically acceptable salt" refers to compounds which are formed from acidifying a solution of the compound of formula in FIG. 2 with suitable physiologically tolerated acids. Suitable physiologically tolerated acids are organic and inorganic acids, such as hydrochloric acid, sulfuric acid, phosphoric acid, acetic acid, citric acid, oxalic acid, malonic acid, salicylic acid, maleic acid, methane sulfonic acid, isothionic acid, lactic acid, gluconic acid, glucuronic acid, amidosulfuric acid, benzoic acid, tartaric acid and pamoaic acid. Typically, such salt forms of the active compound will be provided or mixed prior to use.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts and which are formed with inorganic acids such as, for example, hydrochloric or phosphoric acids, or such organic acids as acetic, oxalic, tartaric, mandelic, and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in creams and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermolysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

B. Oral Administration

In certain embodiments, active compounds may be administered orally. This is contemplated for agents which are generally resistant, or have been rendered resistant, to proteolysis by digestive enzymes. Such compounds are contemplated to include all those compounds, or drugs, that are available in tablet form from the manufacturer and derivatives and analogues thereof.

For oral administration, the active compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Upon formulation, the compounds will be administered in a manner compatible with the dosage formulation and in such amount as is therapeutically effective. The formulations are easily administered in a variety of dosage forms, such as those described below in specific examples.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Figure 3:
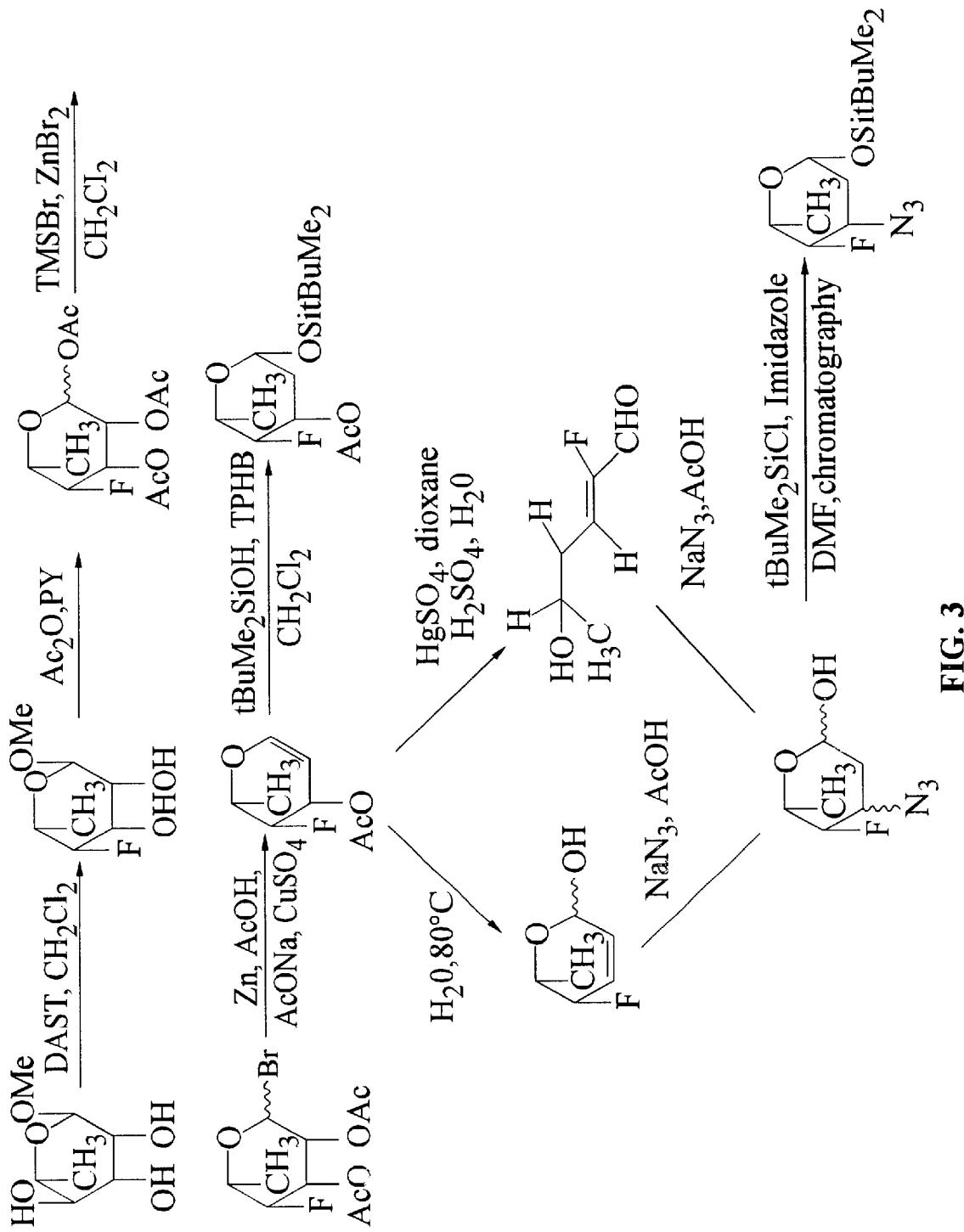
FIG. 3. Synthesis of 4-fluoro-1-O-t-butyldimethylsilly-2,4,6-tetradeoxy-α-L-lyxo-hexopyranose (WP 564), a precursor to WP 715, WP 721, WP 722 and WP 745, and WP 557 and WP 559, both of which are precursors to WP 563.

Synthesis of Exemplary Halogenated Anthracyclines
A. Synthesis of an Exemplary Fluoro-Substituted Sugar Moiety 3-Azido-4-fluoro-1-O-t-butyldimethylsilyl-2,3,4,6-tetradeoxy-α-L-lyxo-hexopyranose (WP 564), 3-O-acetyl-1-O-t-butyldimethylsilyl-4-fluoro-2,4,6-trideoxy-α-L-lyxo-hexopyranose (WP 559), and WP 557, three exemplary 4-fluoro sugar moieties were synthesized as described below and in FIG. 3.

1. Methyl 4,6-Dideoxy-4-fluoro-α-L-talopyranoside (WP 351)

Diethylaminosulfur trifluoride (DAST) (110 mL, 0.833 mol) was added dropwise under nitrogen to a methyl 6-deoxy-α-L-rhamnoside (45 g, 0.253 mol) suspended in anhydrous dichloromethane (900 mL) and cooled down to −40° C. The temperature of the mixture was allowed to rise to room temperature and the reaction mixture was stirred overnight. The next day the reaction mixture was cooled down to −40° C. and methyl alcohol (120 mL) was added dropwise. The reaction mixture was allowed to reach room temperature and then was stirred for 3 hours. Subsequently, the reaction mixture was coevaporated with an excess of a toluene/ethanol (2:1v/v) mixture. The residual oil was cooled in an ice bath and diluted in dichloromethane. Then silicagel (70 g) was added to make a slurry, which was then placed on top of a silicagel column (400 g silicagel), and eluated using dichloromethane/ methanol (95:5 v/v) mixture. Eluent fractions containing one main product were separated, evaporated and then crystallized from ethyl acetate to give 29 g (64%) of methyl 4,6-dideoxy-4-fluoro-α-L-talopyranoside (WP 351).

2. 4,6-Dideoxy-4-fluoro-1,2,3-tri-O-acetyl-L-talopyranose (WP 556)

Methyl 4,6-dideoxy-4-fluoro-α-L-talopyranoside (WP 351) (33 g, 0.183 mol) was dissolved in a mixture of acetic anhydride/ethyl acetate (1:1 v/v, 600 mL) and sulfuric acid (1.5 mL) was added. After 2 hours, the reaction was finished and the reaction mixture was neutralized with a mixture of ice/NaHCO$_3$/aq. Na$_2$CO$_3$ over 4 h. The product was extracted with ethyl acetate and dried with anhydrous Na$_2$SO$_4$. After evaporation of the solvents, the oily residue was dried under reduced pressure to give a crude crystallizing product, which was then purified by crystallization from ethyl ether to give 4,6-dideoxy-4-fluoro-1,2,3-tri-O-acetyl-L-talopyranose (WP 556) (FIG. 3) (50 g, 0.171 mol). Yield: 94%.

3. 3-O-Acetyl-4-deoxy-4-fluoro-L-fucal (WP 557)

4,6-Dideoxy-4-fluoro-1,2,3-tri-O-acetyl-L-talopyranose (WP 556) (16.0 g, 0.0547 mol) was dissolved in anhydrous dichloromethane (120 mL) under nitrogen. Then, TMSBr (36 mL, 0.273 mol) followed by ZnBr$_2$ (4 g, 0.0176 mol) was added. After 10 minutes, the reaction was completed. The reaction mixture was used in the next step without further purification (solution A). Sodium acetate trihydrate (120.0 g) was dissolved in 50% acetic acid (320 mL) and then zinc dust (80 g) followed by saturated aq. CuSO$_4$ (3 mL) was added. The resulting mixture was cooled down to −10° C. The solution A was added with vigorous stirring and the reaction mixture was allowed to rise to the temperature of 15° C. (about 1 hour).

Figure 4:
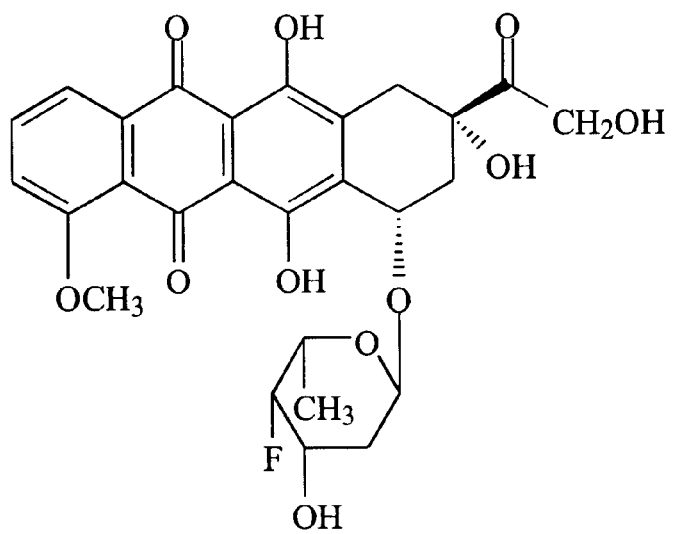
FIG. 4. Structure of 3'-deamino-4'-fluoro-3-hydroxydoxorubicin (WP 563.

The reaction mixture was filtered off and the precipitate was washed with dichloromethane (150 mL) and 50% aq. acetic acid (150 mL). Layers were separated and aqueous layer was further extracted with dichloromethane (500 mL). The organic layers were combined and washed with saturated aq. NaHCO$_3$, and water and dried with anhydrous Na$_2$SO$_4$. Glycal was purified on a silicagel column with the solvents system hexane/ethyl acetate (9:1 v/v) to give the pure product 3-O-acetyl-4-deoxy-4-fluoro-L-fucal (WP 557) (FIG. 3) (8 g, 0.0459 mol). Yield: 84%. WP 557 is a substrate for the production of anthracyclines, such as, WP 563. WP 557 is also useful in making WP 559, which itself can be used to make WP 563 (FIG. 4).

4. 3-Azido-4-fluoro-1-O-t-butyldimethylsilyl-2,3,4,6-tetradeoxy-α-L-lyxo-hexopyranose (WP 564)

To a stirred solution of 3-O-acetyl-4-deoxy-4-fluoro-L-fucal (WP 557) (10 g, 0.0574 mol) in 1,4-dioxane (40 mL) was added 5 mM H$_2$SO$_4$ solution, followed by HgSO$_4$ (0.4 g), at 0° C. Stirring was continued for 1.5 hours at room temperature until no more substrate was detected in the reaction mixture. Then the reaction mixture was neutralized with BaCO$_3$ and the resultant suspension filtered off. Solvents were evaporated to give 11.2 g of a crude aldehyde product. The crude aldehyde was dissolved in water (20 mL), and cooled to 0° C. Then a solution of NaN$_3$ (11.2 g) in water (48 mL), also cooled to 0° C. was added followed by acetic acid (14 mL). Stirring was continued for 2 hours until no traces of substrate were detected in the reaction mixture. Products were extracted with dichloromethane (4×50 mL); extracts were dried with anhydrous Na$_2$SO$_4$ and evaporated. Finally, the residue was coevaporated, first with toluene then with hexane to remove acetic acid and to give azido compounds (12 g).

To the crude azido compounds (12 g) dissolved in DMF (40 mL) was added imidazole (20 g), followed by t-butyldimethylsilyl chloride (18 g). The reaction was left overnight at room temperature. To the reaction mixture, water was added and stirring was continued for 10 minutes. Then the product was extracted with hexane (4×100 mL). Extracts were washed with water, dried with anhydrous Na$_2$SO$_4$, evaporated, and chromatographed on a siligel column using hexane/ethyl ether (95:5 v/v) to give the silyl derivative of 3-azido-4-fluoro-1-O-t-butyldimethylsilyl-2,3,4,6-tetradeoxy-α-L-xylo-hexopyranose (WP 560) (10.16 g, 0.035 mol; Yield: 61%) 3-azido-4-fluoro-1-O-t-butyldimethylsilyl-2,3,4,6-tetradeoxy-α-L-lyxo-hexopyranose (WP 564) (FIG. 3) (2.6 g, 0.09 mol). Yield: 16%. Summary yield of 3-azido-4-fluoro compounds 77%. WP 564 is a substrate for the synthesis of anthracyclines, including WP 715, WP 721, WP 722, and WP 745.

B. Synthesis of 3'-Deamino-4'-fluoro-3-hydroxydoxorubicin (WP 563)

3'-Deamino-4'-fluoro-3-hydroxydoxorubicin (WP 563) has the structure set forth in FIG. 4. It may be synthesized by the following method.

1. 3'-Deamino-4'-fluoro-3'-hydroxydoxorubicin (WP 563)

14-O-tert-Butyldiphenylsilyladriamycinone (615 mg, 0.94 mmol) was dissolved in dry dichloromethane (95 mL) under nitrogen and triphenylphosphine hydrobromide (TPHB) (1.28 g, 3.72 mmol, 0.71 eq) and molecular sieves (3A, 600 mesh, 929 mg) then the sugar WP 557 (910 mg, 5.22 mmol, 5.6 eq.) was added. After 24 hours the reaction was completed. The reaction mixture was diluted with dichloromethane and washed with a 50% solution of sodium bicarbonate in water and dried over anhydrous sodium sulfate. Crude reaction mixture was chromatographed on the silica gel column (40 g, flash) using toluene/acetone 97:3 v/v solvent mixture as eluent to give 648 mg (83.4%) of coupling product.

The coupling product (623 mg, 0.75 mmol) was dissolved in anhydrous dichloromethane (10 ml) and methyl alcohol (60 ml) under nitrogen and 1N sodium methoxide (0.47 ml) was added. After 2 hours, solid carbon dioxide was added and the reaction mixture was diluted with dichloromethane and washed with water (3 times). The crude reaction mixture was chromatographed on the silicagel column using a toluene/acetone gradient (88/12 v/v to 85/15 v/v) as eluent to give 308 mg of 3'-hydroxy product (54.8%).

The 3'-hydroxy product (294.7 mg, 0.39 mmol) was dissolved in dioxane and 1N HCl was added. After 16 hours the reaction mixture was diluted with dichloromethane (400 mL), washed with a saturated solution of sodium bicarbonate (2×100 mL) and water (3×100 mL) and dried over sodium sulfate. The crude reaction mixture was chromatographed on a silicagel column (10 g) in toluene/acetone 75/25 v/v as eluent to give 105 mg of compound WP 563 (shown in FIG. 4), which was precipitated from THF/hexane to give 89 mg (42%) of pure WP 563.

An alternative procedure for the production of WP 563 involves the use of any of a variety of known coupling mechanisms.

C. Synthesis of 4'-Deoxy-4'-fluoro-daunorubicin (WP 715)

Figure 5:
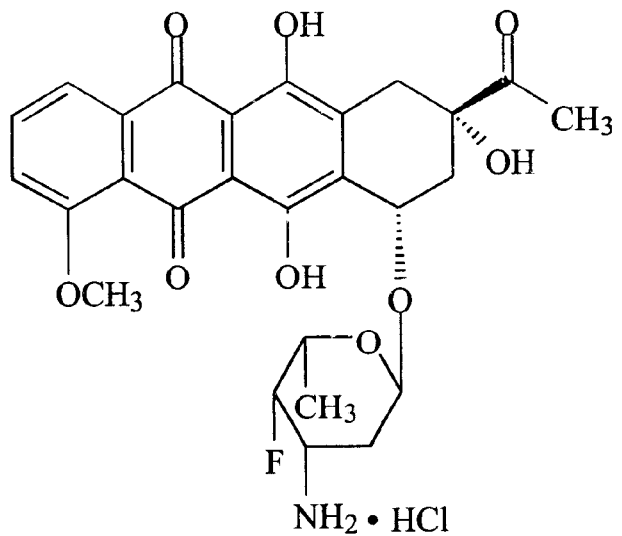
FIG. 5. Structure of 4'-deoxy-4'-fluoro-daunorubicin hydrochloride (WP 715).

4'-Deoxy-4'-fluoro-daunorubicin (WP 715), having the structure shown in FIG. 5 was synthesized in the following manner.

1. Synthesis of 3'-Azido-3'-deamino-4'-deoxy-4'-fluoro-daunorubicin (WP 713)

3-Azido-4-fluoro-1-O-t-butyldimethylsilyl-2,3,4,6-tetradeoxy-α-L-lyxo-hexopyranose (WP 564) (shown in FIG. 3) (1.1 g, 0.0038 mol) was dissolved in dichloromethane (10 mL) and TMSBr (9 mL) was added. After 15 minutes of stirring at room temperature the substrate disappeared. The reaction mixture was evaporated to dryness after which residue was coevaporated twice with fresh portions of dichloromethane, and added immediately to a solution of DMN (0.52 g, .0013 mol), HgO (2.1 g), HgBr$_2$ (0.52 g), and 4 Å sieves (2.1 g) in dichloromethane (60 mL). The reaction mixture was stirred overnight, then filtered. The filtrate was diluted with dichloromethane (80 mL) and washed with 10% aq. KI and water, dried with anhydrous Na$_2$SO$_4$, evaporated, and chromatographed on silicagel column using hexane/ethyl acetate (1:1 v/v) to give pure 3'-azido-3'-deamino-4'-deoxy-4'-fluoro-daunorubicin (WP 713) (0.54 g, 0.00094 mol). Yield: 72%. $^1$H NMR (CDCl$_3$) δ: 14.02, 13.28 (2s, 1H each, OH-6,11), 8.04 (dd, 1H, J=1 Hz, J=8 Hz, H-1), 7,80 (t, 1H, J=8.3 Hz, H-2), 7.42 (dd, 1H, J=8.5 Hz, J=0.9 Hz H-3), 5.63 (d, 1H, J=3.4 Hz, H-1'), 5.31 (m, 1H, H-7), 4.55 (d, 1H, J=50.3 Hz, H-4'), 4.30 (s, 1H, OH-9), 4.18–4.02 (m, 4H, CH$_3$O, H-5'), 3.51 (dddd, 1H, J$_{3',F}$=29.8 Hz, J=12.9 Hz, J=4.9 Hz, J=2 Hz, H-3'), 3.23 (dd, 1H, J=2 Hz, J=18.8 Hz, H-10e), 2.94 (d, 1H, J=18.8 Hz, H-10a), 2.40 (s, 3H, CH$_3$CO),2.31 (dt, 1H, J32 14.9 Hz, J=2.0 Hz, H-8), 2.22–2.12 (m, 2H, H-8, H-2'a), 2.01 (dd, 1H, J=13 Hz, H-2'e), 1.37 (d, 3H, J=5.6 Hz, H-6'). Anal. (C$_{27}$H$_{26}$N$_3$O$_9$F) C, H, N.

2. 4'-Deoxy-4'-fluoro-daunorubicin (WP 714) and its Hydrochloride WP 715

To 3'-azido-3'-deamino-4'-deoxy-4'-fluoro-daunorubicin (WP 713) (0.1 g, 0.175 mmol) dissolved in dichloromethane (5 mL), methanol (15 mL) was added, followed by SnCl$_2$× 2H$_2$O (1 g). However, other methods of reducing azides to amines can be used. The reaction was stirred at room temperature for 5 hours and next poured into a mixture of ethyl acetate and saturated aq. NaHCO$_3$. Then the precipitate was filtered and washed with ethyl acetate and THF. Separately, the aqueous layer was extracted with ethyl acetate, and then all organic layers were combined and washed with water, dried with anhydrous Na$_2$SO$_4$, and chromatographed on a silicagel column with the solvents system dichloromethane/methanol (9:1 v/v) to give 4'-deoxy-4'-fluoro-daunorubicin (WP 714) (0.07 g, 0.128 mmol). Yield: 73%. $^1$H NMR (CDCl$_3$) δ: 14.00, 13.30 (2 bs, 1H each, OH— 6,11), 8.05 (dd, 1H, J=7.6 Hz, H-1), 7.80 (t, 1H, J=8 Hz, H-2), 7.42 (dd, 1H, J=0.8 Hz, J=8.5 Hz, H-3), 5.56 (bs, 1H, H-1'), 5.33 (m, 1H, H-7), 4.58 (bs, 2H, NH$_2$), 4.37 (d, 1H, J$_{F,4'}$=50 Hz, H-4'), 4.17–4.04 (s, m, J=6.6 Hz, H-5', CH$_3$O), 3.22 (dd, 1H, J=1 Hz, J=18.8 Hz, H-10e), 3.10–2.88 (m, 2H, J=18.8 Hz, H-10a, H-3'), 2.42 (s, 3H, CH$_3$CO), 2.32 (dt, 1H, J=14.9 Hz, J=2 Hz H-8), 2.13 (dd, 1H, J=3.9 Hz, J=14.8 Hz, H-8), 1.87–1.73 (m, 2H, H-2), 1.36 (d, 3H, J=6.6 Hz, H-6'). Anal. (C$_{27}$H$_{28}$O$_9$F×0.5 H$_2$O) C,H,N.

Hydrochloride (WP 715) preparation: Deoxy-4'-fluoro-daunorubicin (WP 714) (0.07 g, 0.128 mmol) was dissolved in a methanol-THF mixture and then 1N HCl in ethyl ether (0.135 mmol) was added. The precipitate of hydrochloride was washed with ether and hexane. Anal. (C$_{27}$H$_{28}$NO$_9$F× HCl×1.5 H$_2$0) C, H, N.

D. Synthesis of 4'-Deoxy-4'-fluoro-doxorubicin (WP 721), its Water-soluble Hydrochloride (WP 722), and its Oxalate (WP 745)

Figure 6:
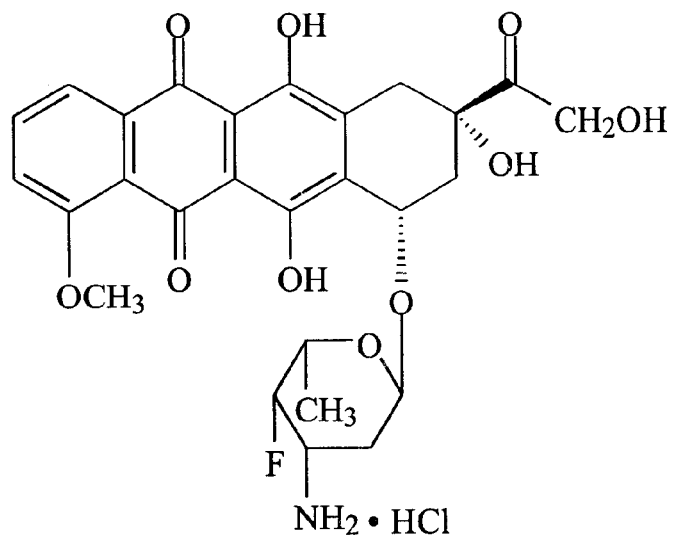
FIG. 6. Structure of WP 722 the water soluble hydrochloride of 4'-deoxy-4'-fluoro-doxorubicin (WP 721).
Figure 7:
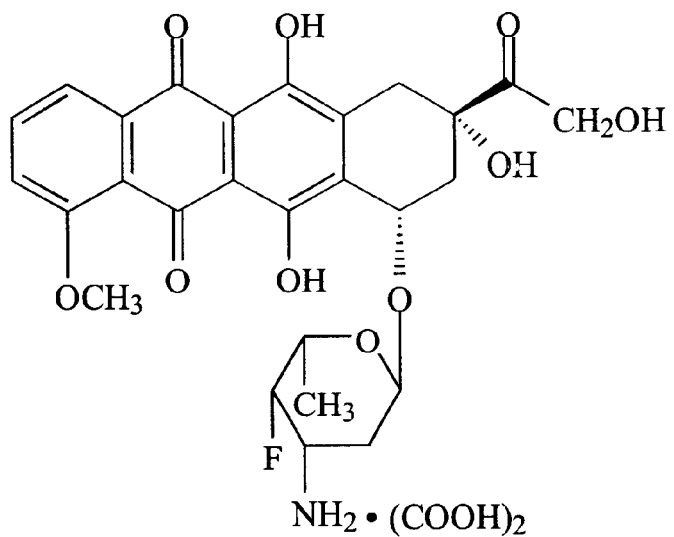
FIG. 7. Structure of WP 745 the oxalate of 4'-deoxy-4'-fluoro-doxorubicin (WP 721).

Synthesis of 4'-deoxy-4'-fluoro-doxorubicin (WP 721), its water-soluble hydrochloride (WP 722), and its oxalate (WP 745) was accomplished by the following method. FIG. 6 shows the structure of WP 722, and FIG. 7 shows the structure of WP 745.

1. Synthesis of 3'-Azido-3'-deamino-4'-deoxy-4'-fluoro-14-O-t-butyldiphenylsilyl-doxorubicin (WP 719)

3-Azido-1-O-t-butyldimethylsilyl-4-fluoro-2,3,4,6-tetradeoxy-α-L-lyxo-hexopyranose (WP 564) (2.0 g, 0.0069 mol) was dissolved in dichloromethane (10 ml), and then TMSBr (2.0 ml) was added. After 15 minutes of stirring at room temperature the substrate disappeared. The reaction mixture was evaporated to dryness after which the residue was coevaporated twice with fresh portions of dichloromethane and then added immediately to a solution of aglycone 14-O-t-butyldiphenylsilyl-adriamycinone (1.0 g, 0.0015 mol), HgO (4.0 g), $HgBr_2$ (1.0 g), and 4A sieves (4.0 g) in dichloromethane (100 mL). The reaction mixture was stirred overnight, then filtered. The filtrate was diluted with dichloromethane (100 mL) and washed with 10% aq. KI, water and dried with anhydrous $Na_2SO_4$. Solvent was evaporated, and the residue was chromatographed on a silicagel column using dichloromethane/methanol (99.5: 0.5 v/v) to give 3'-azido-3'-deamino-4'-deoxy-4'-fluoro-14-O-t-butyldiphenylsilyl-doxorubicin (WP 719) (0.92 g, 0.0011 mol). Yield: 73%. $^1$H NMR ($CDCl_3$) δ: 13.98, 13.20 (2bs, 1H each, OH-6,11), 8.03 (d, 1H, J=7.2 Hz, H-1), 7.78 (t, 1H, J=8.2 Hz, H-2), 7.73–7.67 (m, 5H, from silyl), 7.50–7.36 (m, 6H, from silyl, H-3), 5.53 (d, 1H, J=3.1 Hz, H-1$^1$), 5.22 (bs, 1H, H-7), 4.89 (d, 1H, J=19.7 Hz, H-14), 4.79 (d, 1H, J=19.7 Hz, H-14), 4.43 (d, 1H, $J_{4',F}$=50 Hz, H-4'), 4.08 (s, 3H, $CH_3O$), 3.83 (dq, 1H, $J_{5',F}$=29 Hz, $J_{5',6}$=6.7 Hz, H-5'), 3.43–3.27 (m, 1H, H-3$^1$), 3.02 (d, 1H, J=19 Hz, H-10e), 2.83 (d, 1H, J=19 Hz, H-10a), 2.14–2.04 (m, 3H, J=3.8 Hz, H-8, H-2'), 1.9 (dd, 1H, J=4.8 Hz, J=13.2 Hz, H-2'), 1.17 (d, 3H, J=6.6 Hz, H-6'), 1.13 (s, 9H, tBuSi). Anal. ($C_{42}H_{44}N_3O_{10}FSi×3 H_2O$) C, H, N.

2. 4'-Deoxy-4'-fluoro-14-O-t-butyldiphenylsilyl-doxorubicin (WP 720)

3'-Azido-3'-deamino-4'-deoxy-4'-fluoro-14-O-t-butyldiphenylsilyl-doxorubicin (WP 719) (0.82 g, 0.00101 mol) was dissolved in dichloromethane (25 mL), and then methanol (100 mL), followed by $SnCl_2×2H_2O$ (16 g), was added. The reaction was stirred at room temperature for 5 h, then poured into a mixture of ethyl acetate and saturated aq. $NaHCO_3$. The precipitate obtained was filtered off and washed with ethyl acetate and THF. The aqueous layer was extracted with ethyl acetate, and combined organic layers were washed with water, dried with anhydrous $Na_2SO_4$. Then the solvent was evaporated and the residue chromatographed on a silicagel column using dichloromethane/methanol (8:2 v/v) to give 4'-deoxy-4'-fluoro-14-O-t-butyldiphenylsilyl-doxorubicin (WP 720) (0.4 g, 0.00051 mol). Yield: 50.5%. $^1$H NMR ($CDCl_3$) δ: 13.94, 13.21 (2s, 1H each, OH-6, 11), 8.02 (d, 1H, J=6.6 Hz, H-1), 7.77 (t, 1H, J=8 Hz, H-2), 7.73–7.65 (m, 5H, silyl), 7.40–7.33 (m, 6H, silyl, H-3), 5.45 (bs, 1H, H-1'), 5.21 (bs, 1H, H-7), 4.90 (d, 1H, J=10.2 Hz, H-14), 4.82 (d, 1H, J=9.7 Hz, H-14), 4.25 (d, 1H, $J_{4',F}$=50 Hz, H-4'), 4.07 (s, 3H, $CH_3O$), 3.81 (dq, 1H, $J_{5',F}$=30.4 Hz, $J_{5',6'}$=6.7 Hz, H-5'), 3.0 (d, 1H, J=9.1 Hz, H-10e), 2.95–2.75 (m, 2H, H-10a, H-3'), 2.15–1.95 (m, 2H, H-8), 1.8–1.7 (dd, 1H, J=2 Hz, J=9 Hz, H-2'), 1.15 (d, 3H, $J_{5',6'}$=6.7 Hz, H-6'), 1.12 (s, 9H, tBuSi). Anal. ($C_{42}H_{46}NO_{10}FSi$) C, H, N.

3. 4'-Deoxy-4'-fluoro-doxorubicin (WP 721), its Water-soluble Hydrochloride WP 722 and its Oxalate WP 745

4'-Deoxy-4'-fluoro-14-O-t-butyldiphenylsilyl-doxorubicin (WP 720) (0.4 g, 0.0005 mol) was dissolved in a mixture of THF (25 mL) and methanol (25 mL), and then 1N HCl (35 mL) was added. The reaction was run at room temperature for 3 days after which the reaction mixture was extracted with ethyl acetate. The aqueous layer was separated adjusted to pH 7–8 with aq. $NaHCO_3$, and then extracted with a fresh portion of ethyl acetate. The extract was dried with anhydrous $Na_2SO_4$ and evaporated to give pure product (0.24 g, 0.00045 mol). Yield: 90%. $^1$H NMR ($CDCl_3$) δ: 13.9, 13.25 (2s, 1H each, OH-6,11), 8.03 (d, 1H, J=7 Hz, H-1), 7.77 (t, 1H, J=8 Hz, H-2), 7.35 (d, 1H, J=8.2 Hz, H-3), 5.52 (bs, 1H, H-1'), 5.31 (bs, 1H, H-7), 4.72 (s, 2H, H-14), 4.34 (d, 1H, $J_{4',F}$=50 Hz, H-4'), 4.15–3.85 (m, 4H, $CH_3O$, H-5'), 3.25 (d, 1H, J=19 Hz, H-10e), 3.1–2.8 (m, 2H, H-3', H-10a), 2.30 (d, 1H, J=14.5 Hz, H-8), 2.22–2.07 (dd, 1H, J=4.08 Hz, J=14.5 Hz, H-8), 1.82–1.76 (m, 2H, H-2'a, e) 1.33 (d, 3H, J=6.6 Hz, H-6').

The oxalate (WP 745) was prepared by dissolving the free base in a mixture of dichloromethane and ethyl acetate and then adding of an excess of a saturated solution of oxalic acid in ethyl acetate. The precipitate was then centrifugated and washed with ethyl acetate/ether. Anal. ($C_{27}H_{28}NO_{10}F×(COOH)_2×H_2O$) C, H, N. Hydrochloride WP 722 was prepared using the same procedure as described for daunorubicin analog WP 715.

E. Synthesis of 4',4'-Difluoro-anthracyclines

1. Synthesis of 3-O-Acetyl-1-O-t-butyldimethylsilyl-4,4-difluoro-2,4,6-trideoxy-α-L-hexopyranose (WP 592)

Figure 8:
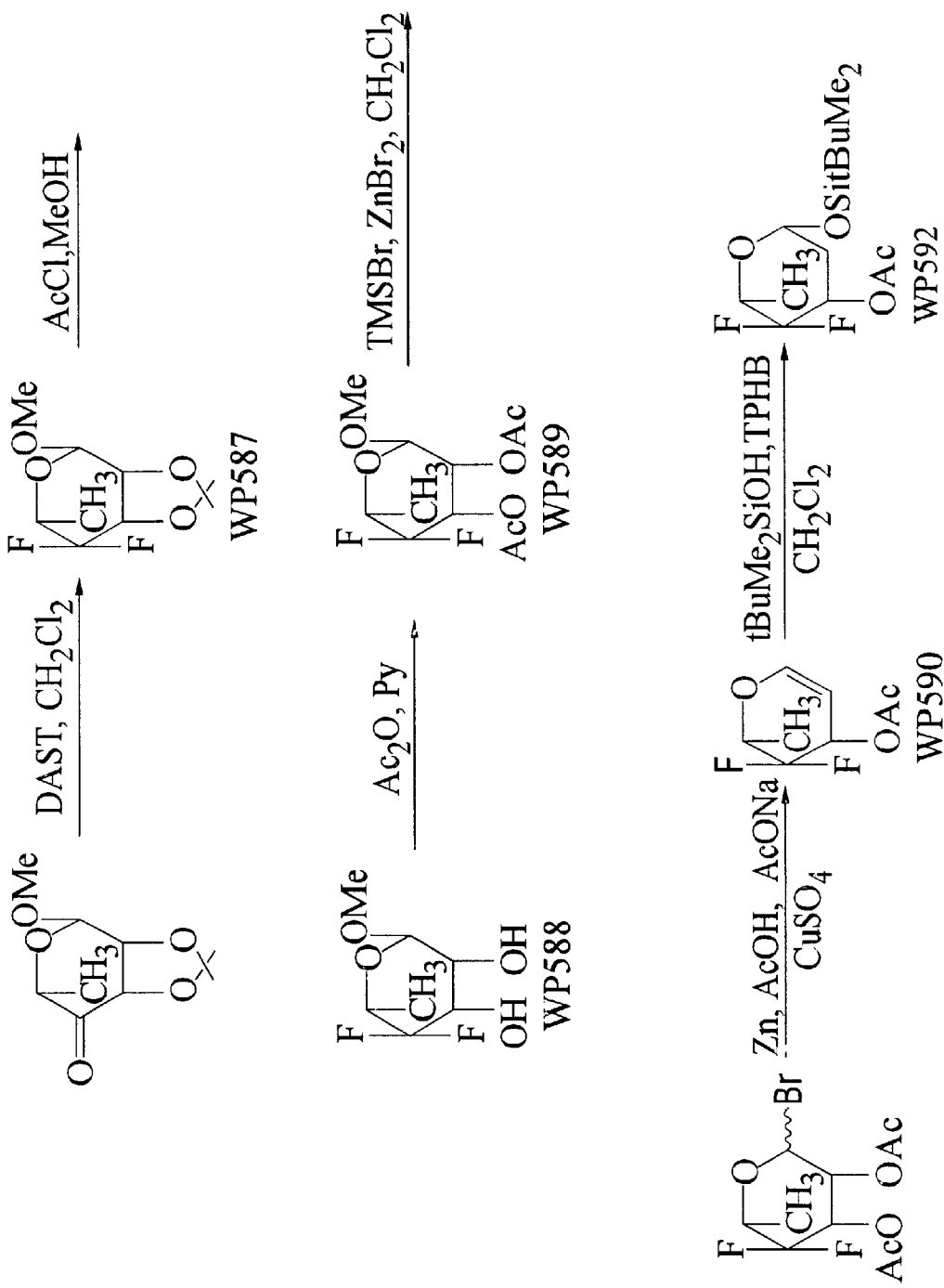
FIG. 8. Synthesis of 4,4-difluoro-L-rhamnose and its derivatives WP 587, WP 588, and WP 589, 4,4-difluoroglycal (WP 590), and 3-O-acetyl-1-O-t-butyldimethylsilyl-4,4-difluoro-2,4,6-trideoxy-β-L-hexopyranose (WP 592).

3-O-acetyl-1-O-t-butyldimethylsilyl-4,4-difluoro-2,4,6-trideoxy-β-L-hexopyranose (WP 592), was prepared in the manner described below and in FIG. 8.

a. Methyl 4,6-Dideoxy-4,4-difluoro-2,3-O-isopropylidene-α-L-hexopyranoside (WP 587)

To methyl 6-deoxy-2,3-O-isopropylidene-α-L-lyxo-hexopyranosid-4-ulose (2 g, 9.2 mmol) suspended in anhydrous dichloromethane (30 mL) and cooled down to –40° C., DAST (6 mL, 45 mmol) was added dropwise under nitrogen. Then the temperature was allowed to rise to room temperature, and the reaction mixture was stirred at 30° C. for 48 hours. The reaction mixture was cooled down to 0° C. and was poured into a mixture of saturated aq. $NaHCO_3$ (80 mL), ice (20 g), and dichloromethane (80 mL). Then layers were separated. The aqueous layer was extracted with dichloromethane (3×100 ml). Then combined extracts were washed with water, dried with anhydrous $Na_2SO_4$, evaporated, and distilled under reduced pressure (70° C./0.04 mmHg) to give crude product 6,4-dideoxy-4,4'-difluoro-2,3-O-isopropylidene-α-methoxy-L-hexopyranoside (WP 587) (2.1 g, 8.8 mmol). Yield: 96%.

An analytical sample was purified on a silicagel column using hexane/ethyl acetate (8:2 v/v). $[α]_D$–7.94° (c=1.5, ethyl acetate). $^1$H NMR ($CDCl_3$) δ: 4.92 (d, 1H, $J_{1,2}$=2.4 Hz, H-1), 4.28 (m, 2H, J=3.2 Hz, H-3, H-2), 3.89 (dq, 1H, $J_{5,F}$=22.9 Hz, $J_{5,6}$=6.5 Hz, H-5), 3.41 (s, 3H, $CH_3O$), 1.57 (s, 3H, $(CH_3)_2C$), 1.38 (s, 3H, $(CH_3)_2C$), 1.33 (d, 1H, $J_{6,5}$=6.5 Hz). Anal. ($C_{10}H_{16}O_4F_2$) C, H.

b. Methyl 4,6-Dideoxy-4,4-difluoro-α-L-hexopyranoside (WP 588) To a solution of methyl 4,6-dideoxy-4,4-difluoro-2,3-O-isopropylidene-α-L-hexopyranoside (WP 587) (2.1 g, 8.8 mmol) in methanol (20 mL) was added acetyl chloride (0.1 mL). The reaction was stirred at room temperature for 4 hours. Triethylamine was then added to neutralize the solution, and the reaction mixture was filtered and evaporated. The crude product was chromatographed on a silicagel column with the solvent system hexane/ethyl acetate (3:2 v/v) to give pure methyl 4,6-dideoxy-4,4-difluoro-α-L-hexopyranoside (WP 588) (1.1 g, 5.6 mmol). Yield 64%. mp 98.5–103.5° C., $[α]_D$402.41° (c=1.5, ethyl acetate). $^1$H NMR ($CDCl_3$) δ: 4.72 (s, 1H, H-1), 4.2–3.7 (m, 3H, , H-3, H-2, H-5), 3.41 (s, 3H, $CH_3O$), 2.88 (d, 1H, J=10 Hz, 3-OH), 2.12 (dd, 1H, J=10.3 Hz, J=3.7 Hz, 2-OH), 1.34 (d, 1H, $J_{6,5}$=6.6 Hz H-6). Anal. ($C_7H_{12}O_4F_2$) C, H.

c. Methyl 2,3-Di-O-acetyl-4,6-dideoxy-4,4-difluoro-α-L-hexopyranoside (WP 589)

A solution of methyl 4,6-dideoxy-4,4-difluoro-α-L-hexopyranoside (WP 588) (1.4 g, 7 mmol), pyridine (10 mL), acetic anhydride (5 mL) and DMAP (5 mg) was stirred at room temperature for 4 hours. The reaction mixture was then cooled in an ice bath, ice (20 g) was added to the mixture, and the mixture was stirred for 20 minutes. The white precipitate was filtered and washed with water and dried under diminished pressure to give 1.0 g of pure methyl 2,3-di-O-acetyl-4,6-dideoxy-4,4-difluoro-α-L-hexopyranoside (WP 589). Additional extraction of the filtrate with ethyl acetate yielded 0.4 g of product. Final yield was 1.4 g (5.6 mmol, 79%). Mp 106–107.5° C., $[\alpha]_D$359.26° (c=1.8, ethyl acetate). $^1$H NMR (CDCl$_3$) δ: 5.44 (ddd, 1H, J=3.8 Hz, J=5.5 Hz, J$_{3,F}$=22 Hz, H-3), 5.32–5.25 (m, 1H, J=3.9 Hz H-2,), 4.68 (s, 1H, H-1), 4.03 (dq, 1H, J$_{5,F}$=22.5 Hz, J$_{5,6}$=6.5 Hz, H-5), 3.39 (s, 3H, CH$_3$O), 2.1 (s, 3H, CH$_3$CO), 2.07 (s, 3H, CH$_3$CO), 1.31 (d, 3H, J$_{6,5}$=6.4 Hz, H-6).

d. 3-O-Acetyl-4,4-difluoro-L-1,5-anhydrohex-1-enitol (WP 590)

Methyl 2,3-di-O-acetyl-4,6-dideoxy-4,4-difluoro-α-L-hexopyranoside (WP 589) (4.3 g, 0.0152 mol) was dissolved in anhydrous dichloromethane (75 mL) under nitrogen and then TMSBr (15 mL, 0.11 mol), followed by ZnBr$_2$ (2.25 g, 0.01 mol), was added. The reaction mixture was then stirred overnight and used in the next step without further purification (solution A).

Sodium acetate trihydrate (45.0 g) was dissolved in 50% acetic acid (200 mL), then zinc dust (22.5 g), followed by saturated aq. CuSO$_4$ (1 mL), was added. The resulting mixture was cooled down to –10° C. Solution A was then added with vigorous stirring and the temperature was allowed to rise to 15° C. in 1 hour. The reaction mixture was filtered off and the precipitate was washed with dichloromethane (50 mL) and 50% aq. acetic acid (50 mL). Filtrate layers were separated, and the aqueous layer was extracted with dichloromethane (500 mL). The organic layers were then combined and washed with saturated aq. NaHCO$_3$, and water, then dried with anhydrous Na$_2$SO$_4$. Glycal WP 590 was distilled under reduced pressure (40° C./0.04 mmHg) to give pure product 3-O-acetyl-4,4-difluoro-L-1,5-anhydrohex-1-enitol (WP 590) (2.5 g, 0.013 mol). Yield: 86%. $[\alpha]_D$ 543.96° (c=1.57, ethyl acetate). $^1$H NMR (CDCl$_3$) δ: 6.42 (d, 1H, J=5.4 Hz, H-1), 5.65–5.35 (m, 1H, H-3), 4.80–4.72 (m, 1H, H-2), 4.18 (dq, 1H, J$_{5,F}$=20.5 Hz, J$_{5,6}$=6.6 Hz, H-5), 2.15 (s, 3H, CH$_3$CO), 1.43 (d, 3H, J$_{6,5}$=6.6 Hz, H-6).

e. 3-O-Acetyl-1-O-t-butyldimethylsilyl-4,4-difluoro-2,4,6-trideoxy-β-L-hexopyranose (WP 529)

To a stirred solution of glycal WP 590 (4.2 g, 0.022 mol) in 1,4-dioxane (40 mL) was added 5 mM H$_2$SO$_4$ (40 mL) solution, followed by HgSO$_4$ (0.1 g) at 0° C. The reaction mixture was stirred at room temperature until all the substrate disappeared from the reaction mixture (overnight). Then the reaction mixture was neutralized using solid BaCO$_3$ and saturated aq. NaHCO$_3$. The suspension obtained was filtered off and washed with dioxane and dichloromethane. The filtrate was then extracted with dichloromethane (4×50 mL) and dried with anhydrous Na$_2$SO$_4$. Solvents were evaporated to give an oily crude product (WP 591). WP 591 (4.4 g) was then dissolved in DMF (30 mL) after which imidazole (6 g), followed by t-Butyldimethylsilyl chloride (5 g), was added. The reaction was stirred overnight at room temperature. Water was added, and the reaction mixture was stirred for 10 minutes. The product was then extracted with hexane (4×80 mL). Extracts were washed with water and dried with anhydrous Na$_2$SO$_4$. Then the solvent was evaporated to dryness to obtain an oily residue. This residue was then purified by using hexane/ethyl ether (98:2 v/v) to give (WP 592) (3.6 g, 0.011 mol). Yield: 50%. $^1$H NMR (CDCl$_3$) δ: 5.16–4.96 (m, 1H, H-3), 4.93 (d, 1H, J=9.2 Hz, H-1), 3.62 (dq, 1H, J$_{5,F}$ =21.7 Hz, J$_{5,6}$=6.4 Hz), 2.2–2.15 (m, 1H, H-2e), 2.14 (s, 3H, CH$_3$CO), 1.94 (m, 1H, H-2a), 1.33 (d, 3H, J$_{6,5}$=6.4 Hz, H-6), 0.88 (s 9H, tBuSi), 1.11 (d, 6H, (CH$_3$)$_2$Si).

2. Synthesis of 3'-Deamino-4'-deoxy-4',4'-difluoro-3'-hydroxy-doxorubicin (WP 600)

Figure 10:
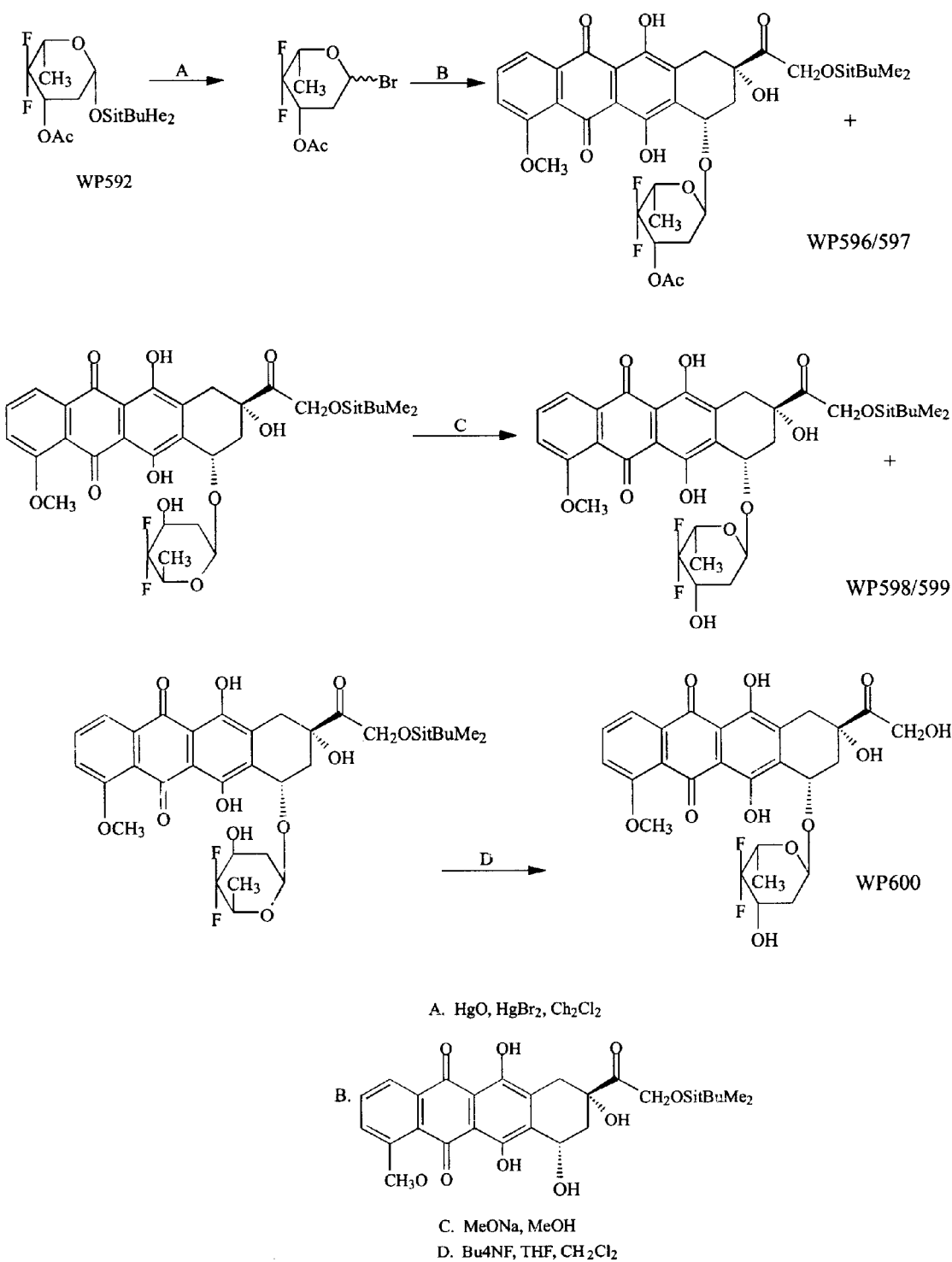
FIG. 10. Synthesis of 3'-deamino-4'-deoxy-4',4'-difluoro-3'-hydroxy-doxorubicin (WP 600).

3-deamino-4'-deoxy-4',4'-difluoro-3'-hydroxy-doxorubicin (WP 600-FIG. 9), was prepared in the manner described below and in FIG. 10.

a. 3'-O-Acetyl-3'-deamino-4'-deoxy-4',4'-difluoro-14-O-t-butyldimethylsilyl-doxorubicin (WP 596/597)

3-O-Acetyl-1-O-t-butyldimethylsilyl-4,4-difluoro-2,4,6-trideoxy-β-L-hexopyranose (WP 592) (1.0 g, 0.003 mol) was dissolved in dichloromethane (10 mL) and TMSBr (15 mL) was added. (Refer to FIG. 10 for a schematic of the reaction.) After 15 minutes of stirring at room temperature, the substrate disappeared. The reaction mixture was evaporated to dryness and coevaporated twice with fresh portions of dichloromethane (5 mL). Then, the prepared mixture was added in three portions to a solution of aglycone 14-O-t-butyldimethylsilyl-adriamycinone (0.42 g, 0.009 mol), HgO (1.8 g), HgBr$_2$ (0.42 g) in dichloromethane (20 mL) over 2 hours. The reaction mixture was diluted with dichloromethane (100 mL) and then filtered. The filtrate was washed with 10% aq. KI, water and dried with anhydrous Na$_2$SO$_4$, the solvent was evaporated, and the residue was chromatographed on a silicagel column using toluene/acetone (98.5:1.5 v/v) to give 3'—O—acetyl-3'-deamino-4'-deoxy-4',4'-difluoro-14-O-t-butyldimethylsilyl-doxorubicin (WP 596/597) (0.23 g, 0.003 mol). Yield: 33%. $[\alpha]_D$256.31° (c=0.018, chloroform/methanol 1:1). Anal. (C$_{35}$H$_{42}$O$_{12}$F$_2$Si) C, H.

b. 3'-Deamino-4'-deoxy-4',4'-difluoro-3'-hydroxy-14-O-t-butyldimethylsilyl-doxorubicin (WP 598/599)

1N CH$_3$ONa in methanol (3×150 mL) was added to 3'-O-acetyl-3'-deamino-4'-deoxy-4',4'-difluoro-14-O-t-butyldimethylsilyl-doxorubicin (WP 596/597) (0.23 g, 0.03 mol) dissolved in dichloromethane (1.5 mL) and methanol (2.5 mL) over 2 hours. The reaction mixture was adjusted to pH 7 with CO$_2$, diluted with dichloromethane (150 mL), washed with water and dried with anhydrous Na$_2$SO$_4$. The solvent was evaporated, and the residue was chromatographed on silicagel column using toluene/acetone (95:5 v/v) to give 3'-deamino-4'-deoxy-4',4'-difluoro-3'-hydroxy-14-O-t-butyldimethylsilyl-doxorubicin (WP 598/599) (0.15 g, 0.022 mol). Yield: 69%. $[\alpha]_D$ 202.64° (c=0.03, chloroform/methanol 1:1). Anal. (C$_{33}$H$_{40}$O$_{11}$F$_2$Si×0.5 H$_2$O) C, H.

c. 3'-Deamino-4'-deoxy-4',4'-difluoro-3'-hydroxy-doxorubicin (WP 600)

To 3'-deamino-4'-deoxy-3'-hydroxy-4',4'-difluoro-14-O-t-butyldimethylsilyl-doxorubicin (WP 598/599) (0.15 g, 0.022 mol) dissolved in THF (25 mL) was added a mixture (27 mL, prepared: THF (20 ml) of dichloromethane (10 ml), pyridine (0.55 mL), 1M Bu$_4$NF in THF (0.5 ml)). After 10 minutes, no more substrate was observed in the reaction mixture. The reaction was then poured into a mixture of 0.1 N HCl (50 mL), dichloromethane (150 mL) and ice (20 g). The aqueous layer was separated and extracted with dichloromethane (2×50 mL). Combined organic layers were washed with water and dried with anhydrous Na$_2$SO$_4$, the solvent was evaporated, and the residue was chromatographed on a silicagel column with toluene/acetone (8:2 v/v) to give 3'-deamino-4'-deoxy-4',4'-difluoro-3'-hydroxy-doxorubicin (WP 600) (0.05 g, 0.009 mol). Yield: 38%. $[\alpha]_D$ 97.68° (c=0.038, chloroform/methanol 1:1). $^1$H NMR (CDCl$_3$) δ: 14.0, 13.22 (2s, 1H each, OH-6,11), 8.04 (d, 1H, J=7.6 Hz, H-1), 7.8 (t, 1H, J=8 Hz, H-2), 7.45–7.25 (m, 1H, J=8.4 Hz, H-3), 5.54 (s, 1H, H-1'), 5.30 (bs, 1H, H-7), 4.76 (s, 2H, H-14), 4.35 (s, 1H, 9-OH), 4.15–3.85 (m, 4H, CH$_3$O, H-5'), 3.3 (d, 1H, J=19 Hz, H-10e), 3.1–2.9 (m, 2H, H-3', H-10a), 2.3–2.08 (m, 3H, J=4 Hz, H-8, H-2'), 2.05–1.95 (dd, 1H, J=3.9 Hz, J=12.9 Hz, H-2'), 1.37 (d, 3H, J=6.6 Hz, H-6').

F. Synthesis of 6'-Fluoro-doxorubicin (WP 743)

Figure 12:
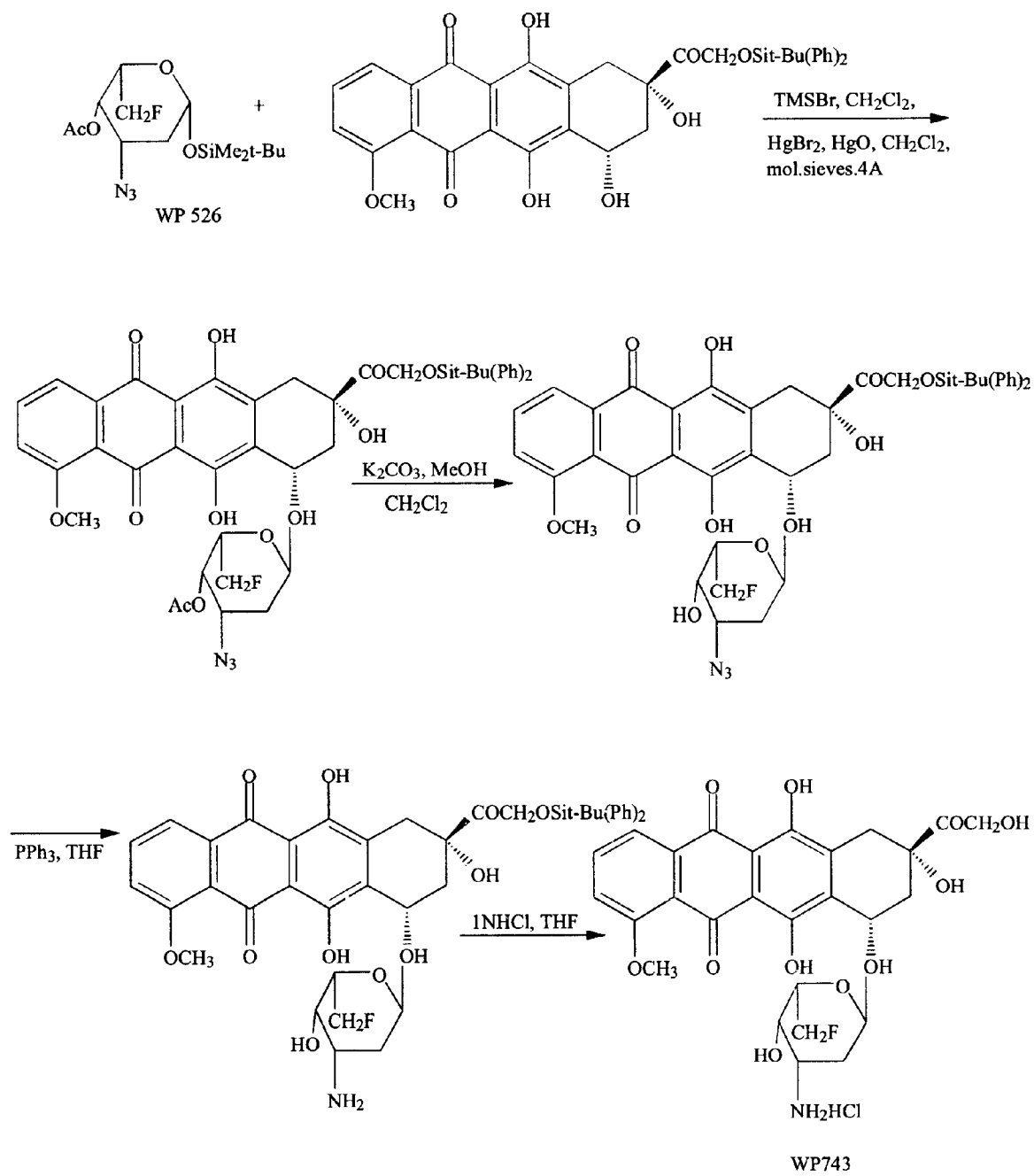
FIG. 12. Synthesis of 6'-fluoro-doxorubicin (WP 743).

6'-Fluoro-doxorubicin (WP 743-FIG. 11), was prepared in the manner described below and in FIG. 12.

4-O-Acetyl-3-azido-6-fluoro-1-O-tert-butyldimethylsilyl-2,3,6-trideoxy-β-L-lyxo-hexopyranose (410 mg; 1.8 mmol) was dissolved in dichloromethane (4 mL). (Refer to FIG. 6 for a schematic of reaction.) Trimethylsilyl bromide (TMSBr) (2.7 mmol; 0.25 mL) was added to this solution, and the reaction mixture was stirred at room temperature until the substrate disappeared. The solvent was removed under diminished pressure and hexanes (10 mL) were added. Solvents were evaporated to dryness, and a second portion of hexanes was added and evaporated. Crude glycosyl bromide was dissolved in dichloromethane (10 mL) and added dropwise to the previously prepared mixture of aglycone (14-O-diphenyl-tert-butylsilyladriamycinone) (410 mg, 1.27 mmol), HgO (1.6 g), $HgBr_2$ (0.4 g) and molecular sieves 4 Å (0.5 g) in dichloromethane (10 mL). The mixture was stirred for 10 minutes (progress of the reaction was monitored by TLC). The reaction mixture was then diluted with dichloromethane (50 mL); the solid residue was filtered off; and the filtrate was washed with 10% solution of potassium iodide (20 mL), then with water (2×10 mL), and dried over $Na_2SO_4$. The drying agent and solvent were removed and the product was purified by column chromatography (Silica gel 60, 230–400 mesh [Merck]) using toluene and then toluene/acetone 98:2 as eluents.

The coupling product (350 mg) was dissolved in methanol/dichloromethane 1:2 v/v (7.5 mL). Solid potassium carbonate (0.5 g) was added to this solution, and the obtained mixture was stirred at room temperature until substrate disappeared. The reaction mixture was diluted with dichloromethane and 1N HCl (4 mL) was added to this solution. The organic layer was then separated and washed with water until neutral. Pure deacetylated product was separated by column chromatography (Silica gel 60 [Merck]), using $CH_2Cl_2$ and $CH_2Cl_2$: acetone (95:5 v/v) as eluents.

Product deacetylated at the 4' position (123 mg, 0.15 mmol) was reacted with triphenylphosphine (77.5 mg, 0.3 mmol) in THF (1 mL) at room temperature overnight. The reaction mixture was diluted with THF (20 mL), 2N $NH_3$ in methanol (2 mL) was added, and the mixture was stirred for another 1 hour. Then, water (50 mL) was added, and the solution was extracted with chloroform (3×15 mL). Combined extracts were washed with water until neutral and dried over $Na_2SO_4$. Free amine was purified by column chromatography on Silica gel 60 (230–400 mesh, Merck) using chloroform and chloroform/methanol (98:2 v/v and 95:5 v/v) as eluents (yield 75%).

The 3'-amino product obtained in the previous step (84 mg) was dissolved in THF (2 mL), 1N HCl (3 mL) was added, and the obtained solution was stirred at room temperature for 40 hours and monitored by TLC. The reaction mixture containing fully unprotected anthracycline was diluted with water (25 mL). After the pH was adjusted to 9 using a saturated $KHCO_3$ solution the product was extracted with chloroform. Combined extracts were dried over $Na_2SO_4$. Fully unblocked WP 743 was then purified by column chromatography on a silica gel using chloroform and chloroform/methanol (95:5 v/v, and 90:1 v/v) as eluents. Chromatographically pure WP 743 was dissolved in methanol (0.5 mL) and 1N solution of a dry HCl in methanol (0.5 mL), followed by diethyl ether was added. WP 743 hydrochloride as a red solid was formed and then filtrated. The red solid was washed with diethyl ether until neutral, then dried under reduced pressure. $^1H$ NMR (methanol-d4,) δ: 7.75, 7.50 (2s, 3H, H-1,2,3), 5.47 (s, 1H, H-1'), 4.9 (s, 1H, H-7) 4.8–4.5 (m, 5H, 14-$CH_2$, H-6'A, 6'B, 5'), 3.99 (s, 3H, OMe), 3.94 (bs, 1H, H-4'), 3.64–3.55 (m, 1H, H-3'), 2.98 (d, 1H, J=18.4 Hz, H-10), 2.71 (d, 1H, J=18.4 Hz, H-10), 2.48 (d, 1H, J=14.66 Hz, H-8), 2.10 (dd, 1H, J:12.93 Hz, J=3.74 Hz, H-2'a), 2.0–1.93 (m, 2H, H-2'e, H-8).

Figure 13:
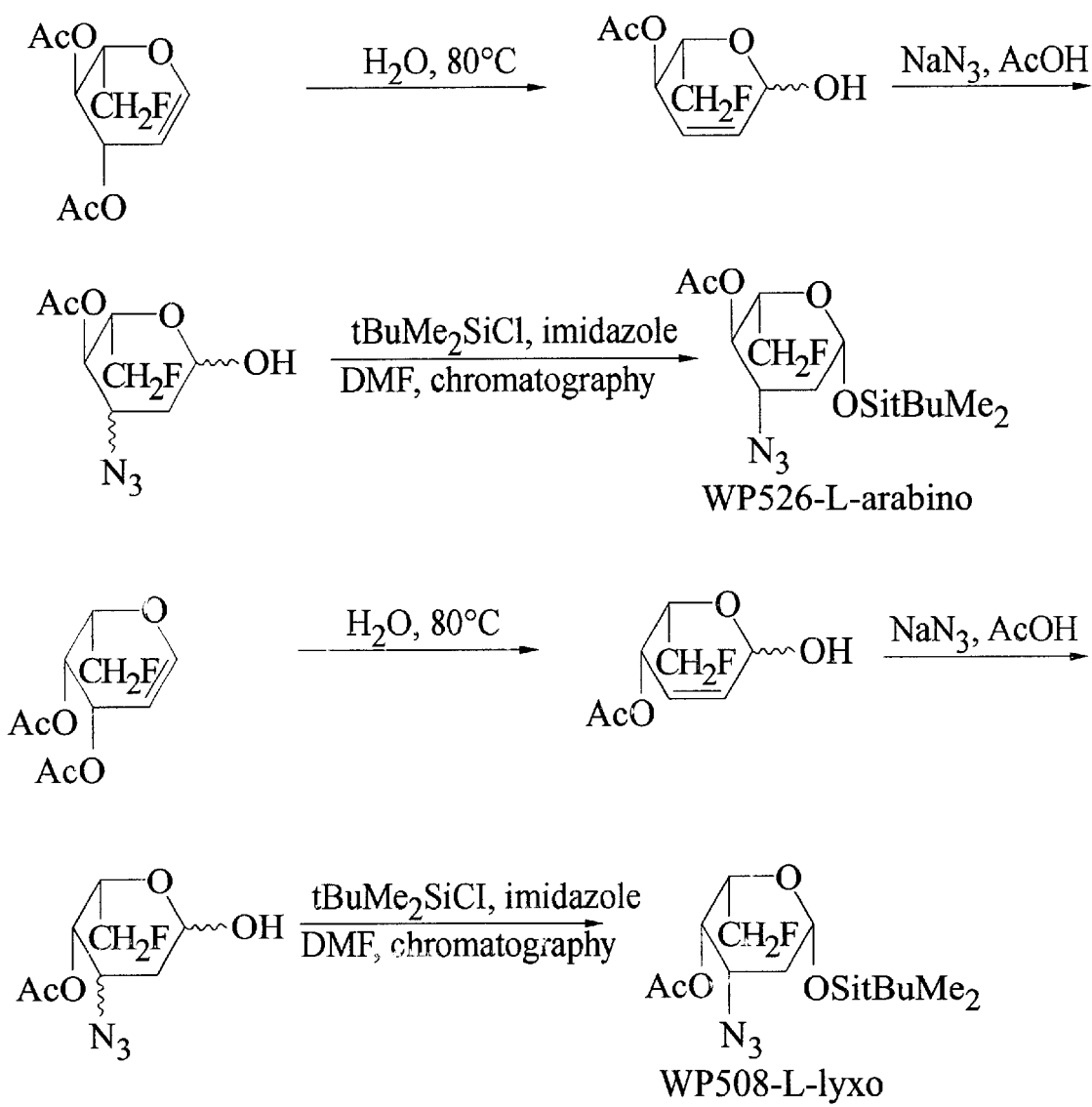
FIG. 13 Synthesis of 6-fluoro-3-azido sugar substrates.

G. Synthesis of 6-Fluoro-3-Azido Sugar Substrates for the Synthesis of 6'-Fluoro Anthracyclines There are many sugar moieties that can be synthesized for use in reactions to produce halo-substituted anthracyclines. In addition to the exemplary moieties described above (for example WP 564 and WP 592), it is possible to make useful 6-fluoro-3-azido sugar substrates using the methods shown in FIG. 13.

A 6-fluoro-3-azido-1-O-tertbutyldimethyl sugar in the lyxo configuration can be obtained starting from two different substrates: 6-fluoro-3,4-diacetyl-L-rhamnal, and 6-fluoro-3,4-diacetyl-L-fucal. In the first step, both starting compounds were hydrolyzed by heating their water solutions up to 80° C., and adding nucleophilic of HN3 to the obtained hydrolysates, followed by silylation of position 1 and selective deprotection of the OH group in position 4.

Water (10 mL) was added to 6-fluoro-3,4-diacetyl-L-fucal (1 mmol), and the mixture was heated up to 70° C. and kept at this temperature for 15 minutes. The reaction mixture was then cooled down to 0° C., and sodium azide (1.5 mmol), followed by glacial acetic acid (0.1 mL) was added. After 1 hour of stirring at 0° C., the second portion of sodium azide and acetic acid (the same amounts) were added, followed by methylene chloride (5 mL), and the mixture was then left stirring at room temperature overnight. Finally, the mixture of azides in the L-lyxo and L-xylo configurations were separated by extraction with methylene chloride.

The crude mixture of azides was then dissolved in DMF (1 mL), tertbutyldimethylchlorosilane (1.2 mmol) and imidazole (1.5 mL) were added, and the mixture was stirred at room temperature overnight. Then, water (15 mL) was added, and products were extracted with hexanes (3×10 mL).

The mixture of crude 1-O-silyl derivatives so obtained was dissolved in methanol (5 mL), and 1M MeONa in MeOH (15 μL) was added at 0° C. The reaction mixture was stirred at 0° C. for 1 hour, 1M HCl (15 μL) followed by water (5 mL) were added, and the obtained solution was then extracted with hexanes (3×5 mL). Pure 4-O-acetyl-3-azido-1-O-dimethyltertbutylsilyl-2,3,6-trideoxy-β-L-lyxopyranoside was separated by column chromatography (Silica Gel 60 (Merck) using hexanes, hexanes/ethyl acetates (98:2 v/v) as eluents.

4-O-Acetyl-3-azido-1-O-dimethyltertbutylsilyl-2,3,6-trideoxy-β-L-lyxopyranoside was also obtained by inverting the configuration in position 4 of 4-O-acetyl-3-azido-1-O-dimethyltertbutylsilyl-2,3,6-trideoxy-β-L-arabinopyranoside, which was obtained according to the above procedure, starting from 6-fluoro-3,4-diacetyl-L-rhamnal.

In the first step, 4-O-acetyl-3-azido-1-O-dimethyltertbutylsilyl-2,3,6-trideoxy-β-L-lyxopyranoside was deacetylated in position 4. Then an easy leaving group (like trifluoromethanosulfonic group) was introduced into this position. The next step was nucleophilic substitution at position 4 using appropriate acetic salts (lithium acetate, tetra-n-butylammonium acetate, and others).

4-O-Acetyl-3-azido-1-O-dimethyltertbutylsilyl-2,3,6-trideoxy-β-L-arabinopyranoside (1 mmol) was dissolved in methanol (10 mL), and potassium carbonate (1.5 mmol) was added. The mixture was stirred at room temperature for 30 minutes, the solid salts were filtered off, and water (10 mL) was added. The mixture was extracted with hexanes (3×10 mL). The combined extracts were washed with water until neutral and dried over a drying agent. The drying agent and solvent were removed, and the product was dried under reduced pressure.

A product with a hydroxyl group in position 4 was dissolved in dichloromethane (5 mL), pyridine (0.5 mL) was added, and the mixture was cooled down to −60° C. Triflic anhydride (1.2 mmol) was then added dropwise to the reaction mixture. The cooling bath was removed, and the mixture was stirred until the temperature in the reaction flask increased to 20° C. The reaction mixture was then washed twice with a 10% solution of sodium acetate. The solvent was removed, the crude product was dried under reduced pressure, and then the crude product was dissolved in DMF (1 mL). Tetrabutylammonium acetate (1.2 mmol) was added to this solution and the reaction mixture was stirred at room temperature for 30 minutes. Water and methylene chloride were added to the reaction mixture. The organic layer was separated, and the water solution was extracted with methylene chloride (2×20 mL). Combined extracts were then washed with water and dried. Pure 4-O-acetyl-3-azido-1-O-dimethyltertbutylsilyl-2,3,6-trideoxy-β-L-lyxopyranoside was separated by column chromatography (Silica Gel 60 Merck) using hexane, hexane/ethyl acetate (98:2 v/v) as eluents.

H. Synthesis of WP 610

Figure 18:
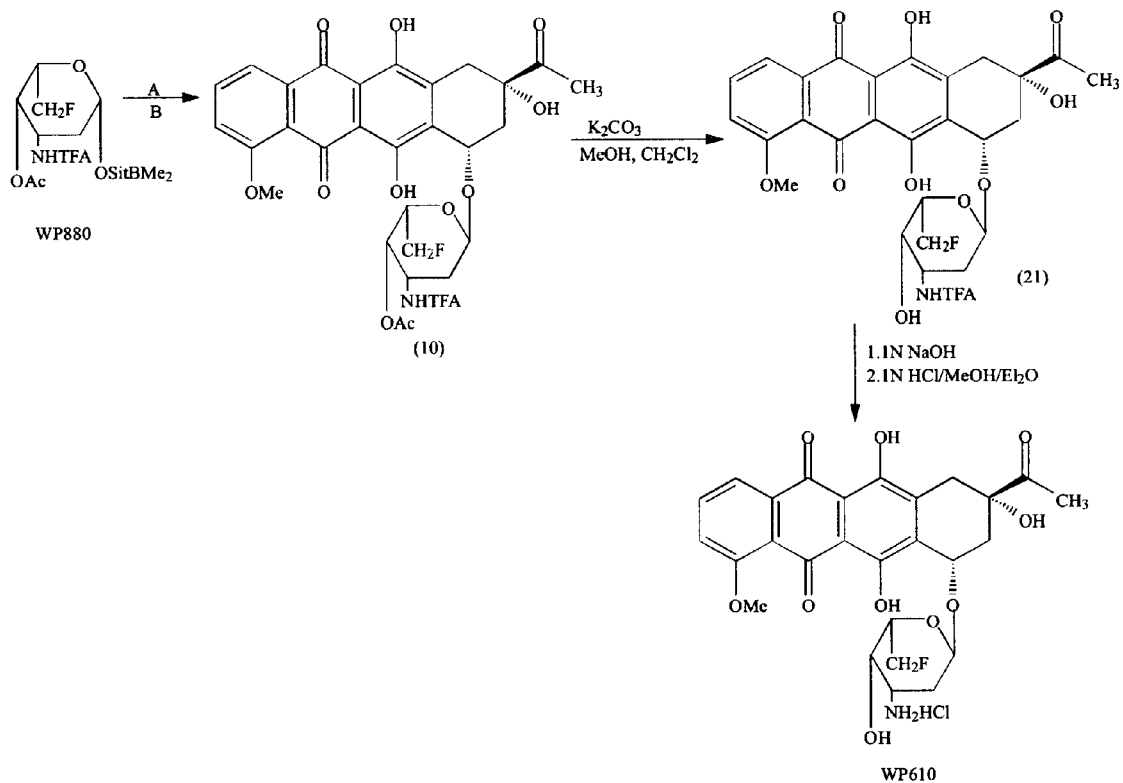
FIG. 18 Synthesis of WP 610.
Figure 18:
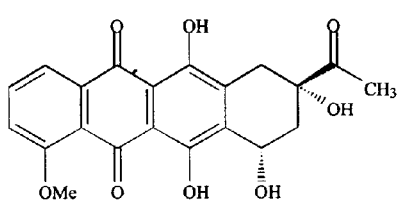

The compound WP 610, as shown in FIG. 19, was synthesized in the manner described below and in FIG. 18.

WP 880 (0.63 mmol) was dissolved in dichloromethane (2.6 mL). Trimethylsilyl bromide (0.79 mmol) was added, and the reaction mixture was stirred at room temperature until all of the substrate was converted into glycosyl bromide. The solvent was then evaporated, and the residue coevaporated with hexanes (3 mL) 3 times. Then, crude glycosyl bromide was dissolved in methylene chloride (3 mL) and added in three portions to the previously prepared mixture of daunomycinone (0.5 mmol), $HgBr_2$ (260 mg), HgO (1 g), and 4 Å molecular sieves. The mixture was stirred at room temperature for 15 minutes, then diluted with methylene chloride (25 mL) and filtered off. The filtrate was then washed with a 10% water solution of K and with water. Pure product (10) was separated by column chromatography on Silica Gel 60 (Merck) with eluents: toluene/acetone (85:15 v/v). The structure of the product (10) was confirmed by $^1$H NMR spectra.

Fully protected antibiotic (10) (0.1 mmol) was dissolved in the mixture of dichloromethane (4 mL) and methanol (2 mL). Solid $K_2CO_3$ (160 mg) was added, and the mixture was stirred at room temperature for 30 minutes. Then, dichloromethane (25 mL), and 1N HCl (1.2 mL) were added to the mixture. The obtained solution was washed with water until neutral and dried over $Na_2SO_4$. Evaporation of the solvents gave one main product (21), deprotected at position 4' that was then purified by column chromatography on Silica Gel 60 (Merck) using $CH_2Cl_2$/acetone (9:1 v/v and 8:2 v/v) as eluent.

Product (21) (0.1 mmol) was then dissolved in dichloromethane (5 mL) and 1N NaOH (0.5 mL) was added to the solution. After 20 minutes of stirring, the reaction mixture was diluted with 1N HCl (5 mL). The organic layer was removed, and the water layer was subsequently extracted with dichloromethane until the organic layer was colorless. Then, the pH of water was adjusted to 9, and the product (free amine of WP 610) was extracted with chloroform. Combined chloroform extracts were washed with water and dried. The drying agent was removed, and the solvent was evaporated. Free amine was dissolved in methanol (1 mL), 1M HCl in MeOH (0.15 mL) was added, and hydrochloride WP 610 was precipitated with diethyl ether as a red solid. The red solid was filtered and washed with diethyl ether until neutral, then dried under reduced pressure. The structure of the product was confirmed by $^1$H NMR spectra and elemental analysis.

EXAMPLE II

Assessment of Antitumor Activity In Vitro

Compounds synthesized using the methods described above can be tested using a standard MTT assay (Green et al., 1984) against human carcinoma sensitive (KB) and multi-drug-resistant (KBV1) cells and MCF-7 and MCF-7/VP-16 resistant cells characterized as having the MRP (multi-drug resistance associated protein) phenotype. The use of an MTT assay using these cells is recognized as an accepted assay for anti-tumor activity by those in the field.

Methods

In vitro cytotoxicity against MCF-7, MCF-7/VP-16, and MCF-7/DOX cell lines. In vitro drug cytotoxicities against human breast carcinoma wild-type MCF-7 and MRP-resistant MCF-7/VP-16 cells were assessed by using the MTT reduction assay, as previously reported (Green et al., 1984). The MTT dye was obtained from Sigma Chemical Co. (St. Louis, Mo.). Cells were plated in 96-well microassay culture plates ($10^4$ cells/well) and grown overnight at 37° C. in a 5% $CO_2$ incubator. Drugs were then added to the wells to achieve a final drug concentration ranging from 0.1 to 50 μg/mL. Four wells were used for each concentration. Control wells were prepared by adding appropriate volumes of calcium- and magnesium-free PBS (pH 7.4). Wells containing culture medium without cells were used as blanks. The plates were incubated at 37° C. in a 5% $CO_2$ incubator for 72 hours. Upon completion of the incubation, 20 μL of stock MTT dye solution (5 mg/mL) was added to each well. After a 4-hour incubation, 100 μL of buffer containing 50% N,N-dimethylformamide and 20% SDS was added to solubilize the MTT formazan. Complete solubilization was achieved by placing the plate in a mechanical shaker for 30 minutes at room temperature. The optical density of each well was then measured with a microplate spectrophotometer at a wavelength of 570 nm. The percent cell viability was calculated by the following equation:

% cell viability=(OD treated wells/OD control wells)×100 where OD is the mean optical density from four determinations. The percent cell viability values were plotted against the drug concentrations used, and the $ID_{50}$ was calculated from the curve. Cytotoxicity experiments were repeated at least three times.

Results and Discussion

Drug resistance, both de novo and acquired, by human tumors is currently a major factor limiting the effectiveness of chemotherapy. Thus, for the in vitro evaluation of fluorinated anthracyclines, the inventors selected and used two sensitive cell lines and variants: a human carcinoma cell line (KB) and a human breast cancer cell line (MCF-7). The multi-drug-resistant (MDR) counterpart of KB (KBVI carcinoma) overexpresses the MDR1 gene that encodes a membrane transport glycoprotein (P-gp); the MCF-7/VP-16 cell line overexpresses the multi-drug-resistant associated protein (MRP); and the MCF-7 cell line which overexpresses the MDR gene. Using this system, the inventors can evaluate a drug's cytotoxic potential against human tumors and at the same time identify compounds that might have unique activity against MDR tumors (Priebe el al, 1993).

Table 2 shows the in vitro evaluation of the cytotoxic properties of fluorinated anthracyclines and doxorubicin (DOX) in KB and KBV1 cells. In sensitive KB cells, WP 715, WP 722 and DOX had similar cytotoxic potentials. However, in the MDR KB-V1 cells, a dramatic difference in cytotoxicity was noted. DOX appeared to be inactive. Its measured $ID_{50}$ was >100 μg/ml, indicating that to achieve a 50% cell kill, the DOX dose has to be increased more than 25 times. The KBV1 cells are also highly resistant to vinblastine and other clinically used MDR drugs. Different results were obtained for WP 743 and WP 600 and particularly for WP 715, WP 722 and WP 563 which appeared to be unusually active against the MDR cells. WP 715's measured resistance index (RI=the ratio of $ID_{50}$ in sensitive cells to $ID_{50}$ in resistant cells) was very small (RI=1.17), and its cytotoxic potential was only minimally reduced when compared with that of DOX, thus indicating that WP 715 can overcome MDR. WP 743 is not as active as the other exemplary compounds against MDR, but it is 6.4 fold more cytotoxic against sensitive KB cells than doxorubicin and also more cytotoxic against multi-drug resistant cells than doxorubicin. WP 563 was the most potent against KBV1.

TABLE 2

In vitro cytotoxicity of fluorinated anthracyclines against sensitive and typical MDR and MRP tumor cell lines

|  | KB μg/ml | KBVI (MDR) | RI | MCF-7 | MCF-7/VP-16 (MRP) | RI | MCF-7/DOX (MDR) | RI |
| --- | --- | --- | --- | --- | --- | --- | --- | --- |
| WP 715 | 3.15 ± 0.9 | 4.1 ± 0.6 | 1.17 | 1.5 ± 1.4 | 2.6 ± 1.6 | 1.7 | 2.2 | 1.46 |
| WP 722 | 2.1 ± 2.5 | 3.3 ± 0.4 | 1.57 | 1.3 ± 1.6 | 4.2 ± 5.0 | 3.23 | 1.9 | 1.46 |
| WP 743 | 0.64 | 41 | 64 | 0.2 | 2.3 | 11.5 | >10 | 50 |
| WP 563 |  | 2.74 ± 2.9 |  |  |  |  |  |  |
| WP 600 |  | 16.9 ± 2.3 |  |  |  |  |  |  |
| DOX | 4.1 ± 0.3 | >100 | >25 | 0.38 | 6.2 | 16.3 | >100 | >263 |

Compounds WP 715, WP 722 and WP 743 were evaluated in sensitive cell line MCF-7 and its multi-drug-resistant counterpart MCF-7/VP-16, which overexpresses the MRP gene; and MCF-7/DOX which overexpresses the MDR gene. Both types of resistance have been shown to have clinical relevance (Norris et al., 1996).

Table 2 shows the results of in vitro evaluation of the cytotoxic properties of halogenated anthracyclines WP 715, WP 722 and WP 743 and doxorubicin (DOX). In sensitive MCF-7 cells, WP 715 and WP 722 were less potent than DOX; however, in the MCF-7/VP-16 cells, a significant increase in cytotoxicity was noticed for all three halogenated anthracyclines when compared with DOX. A dramatic increase in cytotoxicity was observed against MCF-7/DOX cells. The resistance index (RI) of DOX appeared to be 180-fold higher than that of WP 715 and WP 722. The Ris of WP 715 and WP 722 were both below 2 (the RI of WP 743 was 50), indicating that both WP 715 and WP 722 were highly cytotoxic against resistant cells. Therefore, such analogs can be used to overcome MDR and MRP-mediated resistance.

At present, the exact reason for the high activity of these halogenated anthracycline compounds against resistant MDR and MRP cells is not known. However, their unique activity makes them candidates for preclinical and clinical evaluation.

EXAMPLE III

Treatment of Tumors with Halogenated Anthracyclines

Treatment with the halogenated anthracyclines and their respective free amines of the present invention is similar to treatments with other anthracyclines and their derivatives, although some modifications to dosage may be warranted As an example, presented below is the standard treatment with doxorubicin as described in *Remington's Pharmaceutical Sciences*:

Doxorubicin is administered intravenously to adults at a dose of 60 to 75 mg/m$^2$ at 21-day intervals or at 25 to 30 mg/m$^2$ on each of 2 or 3 successive days repeated at 3- or 4-week intervals or 20 mg/M$^2$ once a week. The lowest dose should be used in elderly patients, when there is a history of prior chemotherapy or neoplastic marrow invasion or when the drug is combined with other myelopoiesis-suppressing drugs. The dose should be reduced by 50% if the serum bilirubin lies between 1.2 and 3 mg/dL and by 75% if above 3 mg/dL. The lifetime total dose should not exceed 550 mg/M$^2$ in patients with normal heart function and 400 mg/M$^2$ in patients with abnormal heart function and 400 mg/m$^2$ on each of 3 consecutive days, repeated every 4 weeks. The dosage limits are the same as for with adults. It has been reported that a 96-hour continuous infusion is as effective as and much less toxic than the same dose given by bolus injections.

Of course, modifications of treatment regimens warranted by the unique nature of the halogenated anthracyclines of the present invention are possible and well within the ability of one skilled in the art. Appropriate modifications may be ascertained by following the protocols in the following examples for in vivo testing and developments of human protocols.

EXAMPLE IV

In vivo Prevention of Tumor Development Using Halogenated Anthracvclines

In an initial round of in vivo trials, a mouse model of human cancer with histologic features and metastatic potential resembling those of tumors seen in humans (Katsumata et al., 1995) is used. The animals are treated with halogenated anthracyclines of the present invention to determine the suppression of tumor development.

Halogenated anthracyclines are tested in vivo for antitumor activity against murine leukemia cell lines L1210, P388, and doxorubicin-resistant P388. In conjunction with these studies, the acute and sub-acute toxicities in mice are studied (LD10, LD50, LD90). In a more advanced phase of testing, the antitumor activity of halogenated anthracyclines against human xenografts is assessed and cardiotoxicity studies are done in a rat or rabbit model.

(These studies are based on the discovery that halogenated anthracyclines of the current invention have anticancer activity for MDR cancer cells. The current example proposes using halogenated anthracyclincs to provide a useful preventive and therapeutic regimen for patients with MDR tumors.)

In brief, two groups of mice of a suitable cancer model are treated with doses of halogenated anthracyclines. Several combinations and concentrations of halogenated anthracyclines are tested. Control mice are treated with buffer only.

The effect of halogenated anthracyclines on the development of breast tumors in treated mice versus a control group is then compared by examination of tumor size and histopathologic examination of hematoxylin and eosin stained breast tissue. In light of the chemopreventive potential of WP 715, WP 722 and other halogenated anthracyclines of the present invention, it is predicted that treated mice, will be resistant to tumor development.

EXAMPLE V

Human Treatment with Halogenated Anthracyclines

The following example describes a protocol to facilitate the treatment of cancer patients (for example, those with MDR cancers) using halogenated anthracyclines.

Patients may, but need not, have received previous chemotherapy, radiotherapy or genetherapy. Optimally, the patient exhibits adequate bone marrow function (defined as a peripheral absolute granulocyte count of >2,000/mm$^3$ and a platelet count of 100,000/mm$^3$), adequate liver function (bilirubin 1.5 mg/dl), and adequate renal function (creatinine 1.5 mg/dl).

Halogenated anthracyclines of the present invention will be typically administered orally or parenterally in dosage unit formulations containing standard, well known, non-toxic and physiologically acceptable carriers, adjuvants, and vehicles as desired. The term parenteral as used herein includes subcutaneous, intravenous, intramuscular, and intra-arterial injection and infusion techniques. The halogenated anthracyclines may be delivered to the patient before, after, or concurrently with the other anti-cancer agents.

A typical treatment course may comprise about six doses delivered over a 7- to 21-day period. Upon election by the clinician, the regimen may be continued with six doses every three weeks or less frequently (monthly, bimonthly, quarterly etc.). Of course, these are only exemplary times for treatment, and the skilled practitioner will readily recognize that many other time-courses are possible.

A major challenge in clinical oncology is that many cancers are multi-drug resistant. Thus, one goal of the inventors has been to find ways to improve the efficacy of chemotherapy. In the context of the present invention, the halogenated anthracyclines WP 715 or WP 722 have a surprising activity against such cancers.

To kill MDR cancer cells using the methods and compounds described in the present invention, one will generally contact a target cell with a bisanthracycline of the present invention. These compounds are provided in an amount sufficient enough to kill or inhibit the proliferation of the cell.

It is contemplated that, in certain regimens, the cell will be exposed to agent(s) of the present invention at intervals of about 6 hours to one week. In some situations, however, it may be desirable to significantly extend the intervals between drug administration to several days (2, 3, 4, 5, 6, 7 or more) to even weeks (1, 2, 3, 4, 5, 6, 7, or more).

Regional delivery of halogenated anthracyclines is an efficient method for delivering a therapeutically effective dose to counteract the clinical disease. Likewise, the agents may be directed to a particular affected region. Alternatively, systemic delivery of active agents may be appropriate.

Drugs composed according to the present invention can be administered to the patient directly at the site of the tumor i.e., as a topical treatment of the surface of the cancer. The volume of the drug composition should be sufficient to ensure that all of the tumor is contacted by the halogenated anthracyclines.

In one embodiment of the treatment, the therapeutic compound is simply injected into the tumor. In another embodiment, a catheter is inserted into the site of the tumor, and the cavity is continuously perfused with the therapeutic compound for a desired period of time.

Clinical responses may be defined by accepted measurements of tumor response. For example, a complete response may be defined by the disappearance of all measurable disease for at least a month. A partial response may be defined by a 50% or greater reduction in the sum of the products of perpendicular diameters of all evaluable tumor nodules or at least one month with no tumor sites showing enlargement. A mixed response may be defined by a reduction in the product of perpendicular diameters of all measurable lesions by 50% or more, but disease progression at one or more sites.

Of course, the above-described treatment regimes may be altered in accordance with the knowledge gained from clinical trials such as those described in Example VI below. Those skilled in the art should be able to take the information disclosed in this specification and optimize treatment regimes in light of the clinical trials described in the specification.

EXAMPLE VI

Clinical Trials of the use of Halogenated Anthracyclines in Treating Multi-drug Resistant Cancer This example is concerned with the development of human treatment protocols using the halogenated anthracyclines. These compounds are of use in the clinical treatment of various MDR cancers in which transformed or cancerous cells play a role. Such treatment is a particularly useful tool in anti-tumor therapy, for example, in treating patients with ovarian, breast and lung cancers that are resistant to conventional chemotherapeutic regimens.

The various elements of conducting a clinical trial, including patient treatment and monitoring, is known to those of skill in the art in light of the present disclosure. The following information is being presented as a general guideline for use in establishing WP 715 or WP 722 and other halogenated anthracyclines drugs made by the use of this invention, in clinical trials.

Patients with human metastatic breast and/or epithelial ovarian carcinoma, colon cancer leukemia, or sarcoma are chosen for clinical study. Measurable disease is not required, however the patient must have easily accessible pleural effusion and/or ascites. Further the patients must carry tumors that express MDR phenotype. In an exemplary clinical protocol, patients may undergo placement of a Tenckhoff catheter, or other suitable device, in the pleural or peritoneal cavity and undergo serial sampling of pleural/peritoneal effusion. Typically, one will wish to determine the absence of known loculation of the pleural or peritoneal cavity, creatinine levels that are below 2 mg/dl, and bilirubin levels that are below 2 mg/dl. The patient should exhibit a normal coagulation profile.

In regard to the halogenated anthracyclines drug administration, a Tenckhoff catheter, or alternative device, may be placed in the pleural cavity or in the peritoneal cavity, unless such a device is already in place from prior surgery. A sample of pleural or peritoneal fluid can be obtained, so that baseline cellularity, cytology, LDH, and appropriate markers in the fluid (CEA, CA15-3, CA 125, p185) and in the cells (E1A, p185) may be assessed and recorded.

In the same procedure, halogenated anthracyclines may be administered. The administration may be in the pleural/peritoneal cavity, directly into the tumor, or in a systemic manner. The starting dose may be 0.5 mg/kg body weight. Three patients may be treated at each dose level in the absence of grade >3 toxicity. Dose escalation may be done by 100% increments (0.5 mg, 1 mg, 2 mg, 4 mg) until drug related Grade II toxicity is detected. Thereafter, dose escalation may proceed by 25% increments. The administered dose may be fractionated equally into two infusions, separated by 6 hours if the combined endotoxin levels determined for the lot of bisanthracycline exceed 5EU/kg for any given patient.

The halogenated anthracyclines may be administered over a short infusion time or at a steady rate of infusion over a 7- to 21-day period. The bisanthracycline infusion may be administered alone or in combination with the anti-cancer drug. The infusion given at any dose level is dependent upon the toxicity achieved after each. Hence, if Grade II toxicity was reached after any single infusion, or at a particular period of time for a steady rate infusion, further doses should be withheld or the steady rate infusion stopped unless toxicity improves. Increasing doses of halogenated anthracyclines in combination with an anti-cancer drug is administered to groups of patients until approximately 60% of patients show unacceptable Grade III or IV toxicity in any category. Doses that are ⅔ of this value could be defined as the safe dose.

Physical examination, tumor measurements, and laboratory tests should, of course, be performed before treatment and at intervals of about 3–4 weeks later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum should be monitored, e.g. CEA, CA 15-3, p185 for breast cancer, and CA 125, p185 for ovarian cancer.

To monitor disease course and evaluate the anti-tumor responses, it is contemplated that the patients should be examined for appropriate tumor markers every 4 weeks, if initially abnormal, with twice weekly CBC, differential and platelet count for the 4 weeks; then, if no myelosuppression has been observed, weekly. If any patient has prolonged myelosuppression, a bone marrow examination is advised to rule out the possibility of tumor invasion of the marrow as the cause of pancytopenia. Coagulation profile shall be obtained every 4 weeks. An SMA-12-100 shall be performed weekly. Pleural/peritoneal effusion may be sampled 72 hours after the first dose, weekly thereafter for the first two courses, then every 4 weeks until progression or off study. Cellularity, cytology, LDH, and appropriate markers in the fluid (CEA, CA15-3, CA 125, p185) and in the cells (p185) may be assessed. For an example of an evaluation profile, see Table 3. When measurable disease is present, tumor measurements are to be recorded every 4 weeks. Appropriate radiological studies should be repeated every 8 weeks to evaluate tumor response. Spirometry and DLCO may be repeated 4 and 8 weeks after initiation of therapy and at the time study participation ends. A urinalysis may be performed every 4 weeks.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least one month with no tumor sites showing enlargement. Similarly, a mixed response may be defined by a reduction of the product of perpendicular diameters of all measurable lesions by 50% or greater with progression in one or more sites.

TABLE 3

Evaluations before and during therapy.

| EVALUATIONS | PRE-STUDY | TWICE WEEKLY | WEEKLY | EVERY 4 WEEKS | EVERY 8 WEEKS |
|---|---|---|---|---|---|
| History | X | | | X | |
| Physical | X | | | X | |
| Tumor Measurements | X | | | X | |
| CBC | X | $X^1$ | X | | |
| Differential | X | $X^1$ | X | | |
| Platelet Count | X | $X^1$ | X | | |
| SMA12-100 (SGPT, Alkaline Phosphatase, Bilirubin, Alb/Total Protein) | X | | X | | |
| Coagulation Profile | X | | | X | |
| Serum Tumor markers (CEA, CA15-3, CA-125, Her-2/neu) | X | | | $X^3$ | |
| Urinalysis | X | | | X | |
| X-rays: | | | | | |
| Chest | X | | $X^4$ | | |
| Others | X | | | | X |
| Pleural/Peritoneal Fluids: (cellularity, cytology, LDH, tumor markers, E1A, HER-2/neu) | X | | $X^5$ | X | |
| Spirometry and DLCO | X | | | $X^6$ | $X^6$ |

$^1$For the first 4 weeks, then weekly, if no myelosuppression is observed.
$^2$As indicated by the patient's condition.
$^3$Repeated every 4 weeks if initially abnormal.
$^4$For patients with pleural effusion, chest X-rays may be performed at 72 hours after first dose, then prior to each treatment administration.
$^5$Fluids may be assessed 72 hours after the first dose, weekly for the first two courses and then every 4 weeks thereafter.
$^6$Four and eight weeks after initiation of therapy.

EXAMPLE VII

Clinical Trials of the use of Halogenated Anthracyclines in Treating Alzheimer's Disease This example is concerned with the development of human treatment protocols for the treatment and prevention of Alzheimer's disease using the compounds developed in the present invention. The halogenated anthracyclines synythesized in this invention can prevent amyloidosis, alone or in combination with other treatments for plaque related diseases. These treatments will also be of use in the clinical treatment of various diseases in which amyloidosis and plaque formation play a role, including Alzheimer's disease, Prion-disease, Downs syndrome and other disease listed in Table 4 herein below.

TABLE 4

Amyloidogenic proteins and pathological states associated therewith. Exemplary Genbank sequences for peptides are listed and incorporated herein by reference.

| Peptide | Pathology |
|---|---|
| β-amyloid peptide | Alzheimer's Disease |
| | Down's Syndrome |
| | Dutch-Type Hereditary Cerebral Hemorrhage Amyloidosis |
| Amyloid A (Genbank P22614; P02735; J03474; D32001; A38974; I39456; S48983; X51442) | Reactive (Secondary) Amyloidosis Familial Mediterranean Fever Familial Amyloid Nephropathy With Urticaria And Deafness (Muckle-Wells Syndrome) |
| amyloid kappa L-chain (Genbank:P04430; P01617; L33854) or amyloid lambda L-chain | Idiopathic (Primary) or Macroglobulinemia-Associated Myeloma |
| A beta 2M | Chronic Hemodialysis |
| ATTR | Familial Amyloid Polyneuropathy (Portuguese, Japanese, Swedish) |
| | Familial Amyloid Cardiomyopathy (Danish) |
| | Isolated Cardiac Amyloid |
| | Systemic Senile Amyloidosis |
| AIAPP (Genbank X68830; P10997) or amylin (Genbank: M27503) | Adult Onset Diabetes Insulinoma |
| atrial naturetic factor | Isolated Atrial Amyloid |
| procalcitonin (Genbank P06881) | Medullary Carcinoma Of The Thyroid |
| gelsolin (Genbank: U28044; M36927; X75629; X75630) | Familial Amyloidosis (Finnish) |
| cystatin C (Genbank: X52255; M58167, M58169) | Hereditary Cerebral Hemorrhage With Amyloidosis (Icelandic) |
| AApoA-I (Genbank P02647; J00098) | Familial Amyloidotic Polyneuropathy (Iowa) |
| AApoA-II | Accelerated Senescence In Mice |
| AScr or PrP-27 (Genbank: P27177; P23907; P13852; P10279; P04925; P04156; S53625; S53624 | Scrapie Creutzfeldt-Jacob Disease, Gerstmann-Straussler-Scheinker Syndrome, Bovine Spongiform Encephalitis |

The various elements of conducting a clinical trial, including patient treatment and monitoring, will be known to those of skill in the art in light of the present disclosure. The following information is being presented as a general guideline for use in the treatment of amyloidosis, alone or in combination with other drugs in clinical trials.

Patients with an amyloidogenic disease or at risk of contracting such a disease are chosen for clinical study will typically have failed to respond to at least one course of conventional therapy. Measurable disease is not required. The only criterion is that these patients have or are suspected to have amyloidogenic plaques and are or have undergone fibrillogenesis.

In an exemplary clinical protocol, patients may undergo placement of a catheter, or other suitable delivery device, in a cavity will provide an effective means of delivering a therapeutic compounds of the present invention and for sampling the individual for the presence of plaque-forming amyloidogenic peptides. In the same procedure, the halogenated anthracycline compounds developed in this invention may be administered alone or in combination with other therapeutic drugs that are commonly used in the treatment of Alzheimer's Disease and other amyloidogenic diseases. The administration may be regional, directly into the fibrillogenic plaque, or in a systemic manner.

The starting dose may be 0.5 mg/kg body weight. Three patients may be treated at each dose level in the absence of grade ≧3 toxicity. Dose escalation may be done by 100% increments (0.5 mg, 1 mg, 2 mg, 4 mg) until drug related grade 2 toxicity is detected. Thereafter dose escalation may proceed by 25% increments. The administered dose may be fractionated equally into two infusions, separated by six h if combined with a second drug for any given patient.

The halogenated anthracycline derivatives, and any other anti-amyloidogenic drug used in combination, may be administered over a short infusion time or at a steady rate of infusion over a 7 to 21 day period. The halogenated anthracyclines may be administered by infusion, alone or in combination with the other anti-amyloidogenic drug. The infusion given at any dose level will be dependent upon the toxicity achieved after each administration. Hence, if Grade II toxicity was reached after any single infusion, or at a particular period of time for a steady rate infusion, further doses should be withheld or the steady rate infusion stopped unless toxicity improved. Increasing doses of the halogenated anthracyclines alone or in combination with another anti-amyloidogenic drug will be administered to groups of patients until approximately 60% of patients show unacceptable Grade III or IV toxicity in any category. Doses that are ⅔ of this value could be defined as the safe dose.

Physical examination, plaque measurements, and laboratory tests should, of course, be performed before treatment and at intervals of about 3–4 wk later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum should be monitored.

To monitor disease course and evaluate the anti-plaque responses, it is contemplated that the patients should be examined for appropriate plaques and markers of disease every 4 wk, if initially abnormal. When measurable disease is present, plaque size measurements are to be recorded every 4 wk. Appropriate CAT scanning studies should be repeated every 8 wk to evaluate plaque response. An urinalysis may be performed every 4 wk.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable fibrillogenic plaques or at least 1 month with no plaque sites showing enlargement. Similarly, a mixed response may be defined by a reduction of the product of perpendicular diameters of all measurable lesions by 50% or greater with progression in one or more sites.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Arcamone F., Doxorubicin. Anti-Cancer Antibiotics. New York: Academic Press, 1981.
Bell et al., *J. Clin. Oncol.*, 3:311, 1985
Bertino, *J. Clin. Oncol.*, 3:293, 1985
Bodley, et al., *Cancer Res.*, 49:5969–5978, 1989.
Bodley et al., *Cancer Res.*, 49:5969.
Booser D J and Hortobagyl G N., "Anthracycline Antibiotics in Cancer Therapy. Focus on Drug Resistance", *Drugs*, 47:223–258, 1994.
Bradley et al., *Biochem. Biophys. Acta.*, 948:87, 1988.
Capranico et al., "Sequence-Selective Topoisomerase II Inhibition by Anthracycline Derivatives in SV40 DNA: Relationship with DNA Binding Affinity and Cytotoxicity", *Biochem*, 29:562–569, 1990.
Curt et al., *Cancer Treat. Rep.*, 68:87, 1984.
Danks et al., *Cancer Res.*, 47:1297, 1987.
Denny et al., "Potential Anti-tumor Agents. 39. Anilino Ring Geometry of Amsacrine and Derivatives: Relationship to DNA binding and Anti-tumor Activity", *J. Med. Chem.*, 26(11):1625–1630, 1983.
Dervan P. *Science*, 232:464–471, 1986.
Fojo et al., *P.N.A.S.*, 84:265, 1987.
Ganapath, et al., *Br. J. Cancer*, 60:819, 1989.
Gianni et al., *Blood*, 86(3):855–861, 1995.
Goldie et al., *Cancer Res.*, 44:3643, 1984.
Goldie et al., *Cancer Treat. Rep.*, 63:1727, 1979.
Green et al., *J. Immunol. Methods*, 70:257–268, 1984.
Gros et al., *Nature*, 323:728, 1986
Israel et al., *Cancer Treat Rev.* Dec; 14(3–4):163–7, 1987.
Israel et al., *Cancer Chemother. Pharmacol.*, 25:177, 1989.
Katsumata et al., "Prevention of Breast Tumor Development In Vivo by Down-Regulation of the p185$^{neu}$ Receptor", *Nature Med.*, 1:644–648, 1995.
Kolate, *Science*, 231:220, 1986.
Lown J W, "Targeting the DNA Minor Groove for Control of Biological Function:
Progress, Challenges and Prospects", *Chemtracts—Org. Chem.*, 6:205–237, 1903.
Lown J W, "*Anthracycline and Anthracenedione-Based Anticancer Agents*, Bioactive Molecules, Vol. 6, Amsterdam: Elsevier, 1988.
Merlini et al., *Proc. Natl. Acad. Sc. USA*, 92:2959–2963.
Norris et al., "Expression of the gene for multidrug-resistance-associated protein and outcome in patients with neuroblastoma", *N. Engl. J. Med*, 334:231–238, 1996.
Nowell, *Cancer Res.*, 46:2203, 1986.
Pommier et al., *Cancer Res.*
Priebe et al., "3'-Hydroxy-esorubicin halogenated at C-2'", *J. Antibiot*, 45:386–393, 1992.
Priebe et al., "Removal of the basic center from doxorubicin partially overcomes multidrug resistance and decreases cardiotoxicity", *Anti-Cancer Drugs*, 4:37–48, 1993.
Priebe W, "Anthracycline Antibiotics. Novel Analogues, Methods of Delivery, and Mechanisms of Action", Washington, DC: American Chemical Society, 1995.
Priebe W. "Mechanism of Action-Governed Design of Anthracycline Antibiotics: A "Turn-Off/Turn-On" Approach", *Current Pharmaceutical Design*, 1:51–68, 1995.
Rubinstein et al., "Comparison of In Vitro Anti-Cancer-Drug-Screening Data Generated with A Tetrazolium Assay Versus a Protein Assay Against a Diverse Panel of Human Tumor Cell Lines", *J. Nat'l. Cancer Inst.*, 82:1113–1120, 1990.
Stryer, "Biochemistry", Freeman and Co., 1981.
Sweatman et al, *J. Cell. Pharmacol.*, 1:95–102.
Traganos et al., *Cancer Res.*, 45:6273, 1985.
Tragliavini et al., *Science*, 276:1119–1122, 1997
Wakelin L P G, *Medicinal Research Rev*, 6:275–340, 1986.
Young etal., *N. Engl. J. Med.*, 312:692, 1985.
U.S. Pat. No. 4,263,428 Apr. 21, 1981.
U.S. Pat. No. 4,345,070, Aug. 17, 1982.
U.S. Pat. No. 4,438,105, Mar. 20, 1984.

What is claimed is:

1. A compound having the formula:

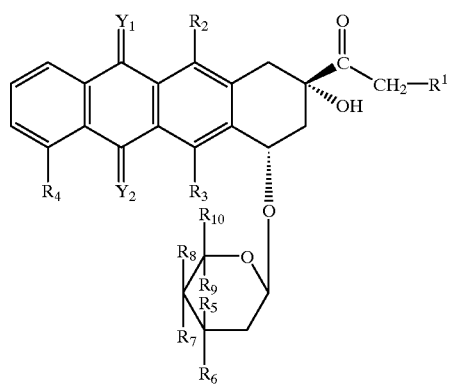

wherein:

- $R^1$ is a hydrogen (—H) group, a hydroxyl group (—OH), a methoxy group (—OCH$_3$), an aryl group having 6–20 carbon atoms, a fatty acyl group having the general structure —O—CO(CH$_2$)$_n$CH$_3$, wherein n=an integer from 1 to about 20, or a fatty acyl group having the general structure —O—CO(CH$_2$)$_l$(CH=CH)$_m$(CH$_2$)$_n$CH$_3$, wherein l is an integer between 1 to 3, m is an integer between 1 and about 6, and n is an integer between 1 to about 9;

- each of $R^2$ and $R^3$ is, independently of the other, a hydrogen (—H) group, a hydroxyl group (—OH), a methoxy group (—OCH$_3$) or a double bonded oxygen moiety;

- $R^4$ is a hydrogen (—H) group, a hydroxyl group (—OH), a methoxy group (—OCH$_3$), or a halide;

- Each of $Y^1$ and $Y^2$ is, independently of the other, a hydrogen (—H) group; a hydroxyl group (—OH); a methoxy group (—OCH$_3$); or a double bonded oxygen, sulphur, or nitrogen group;

- $R^5$ is —H, —OH, —OR$^{11}$, —SH, —SR$^{11}$, —NH$_2$, or —NHR$^{11}$;

- $R^6$ is —H, —OH, —OR$^{11}$, —SH, —SR$^{11}$, —NH$_2$, —NR$^{11}$, or —NHR$^{11}$;

- $R^7$ is —H, —OH, —OR$^{11}$, —SH, —SR$^{11}$, —NH$_2$, —NHR$^{11}$, F, I, Br, or Cl, with the proviso that $R^7$ can be I only when $R^6$ is —OH or —SH;

- $R^8$ is —H, —OH, —OR$^{11}$, —SH, —SR$^{11}$, —NH$_2$, —NHR$^{11}$, F, I, Br, or Cl;

- $R^9$ is CH$_3$, CH$_2$F, CH$_2$I, CH$_2$Br, or CH$_2$Cl;

- $R^{10}$ is H, F, I, Br, or Cl,

- wherein $R^{10}$ must be a halogen or $R^9$ must be a methyl halide; and

- $R^{11}$ is a methyl group, an aryl group having 6–20 carbon atoms, a fatty acyl group having the general structure —CO(CH$_2$)$_n$CH$_3$ wherein n an integer from 1 to about 20, or a fatty acyl group having the general structure —CO(CH$_2$)$_l$(CH=CH)$_m$(CH$_2$)$_n$CH$_3$ wherein l is an integer between 1 to 3, m is an integer between 1 and about 6, and n is an integer between 1 to about 9.

2. A compound having the formula:

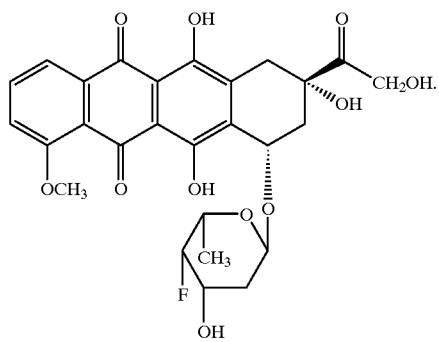

3. A compound having the formula:

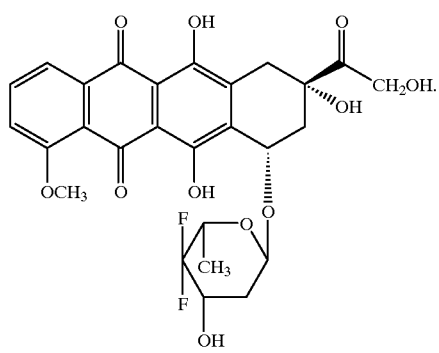

4. The compound of claim 1, having the formula:

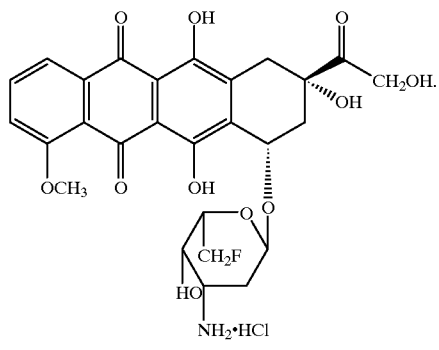

5. The compound of claim 1, having the formula:

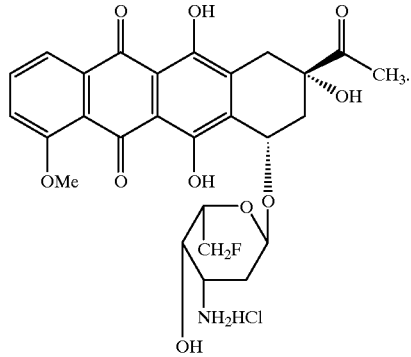

6. A sugar having the structure:
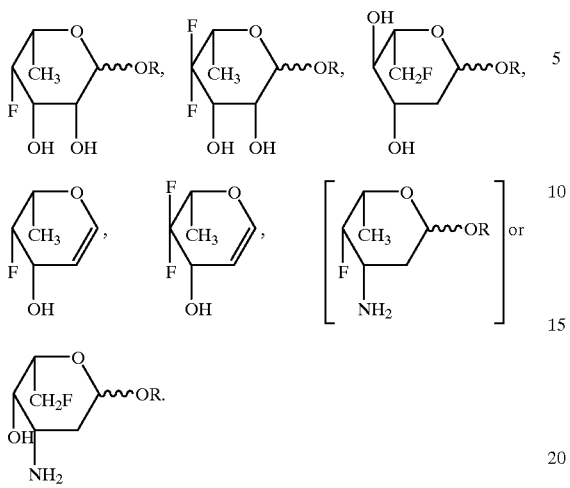
wherein R is a leaving group
7. The compound of claim 1, further defined as having one of the formulae:
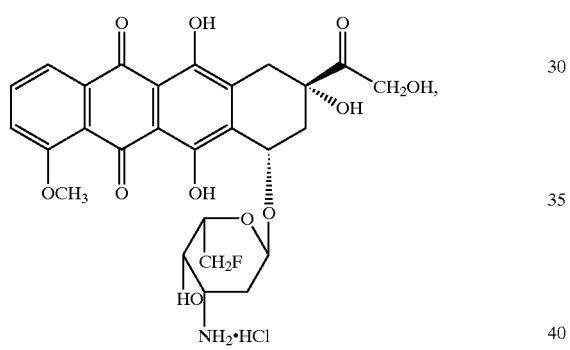
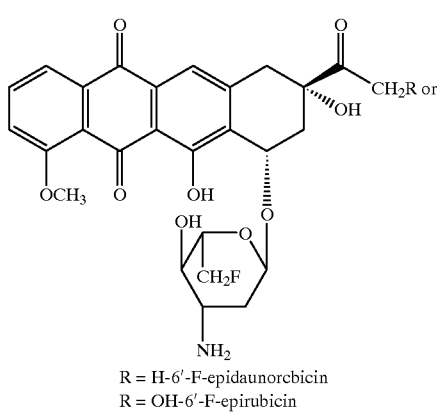
R = H-6'-F-epidaunorcbicin
R = OH-6'-F-epirubicin
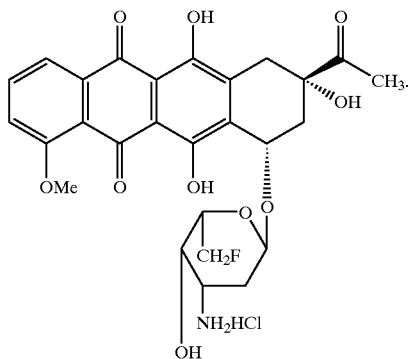
* * * * *

UNITED STATES PATENT AND TRADEMARK OFFICE
CERTIFICATE OF CORRECTION

PATENT NO.    : 6,355,784 B1  Page 1 of 1
DATED         : March 12, 2002
INVENTOR(S)   : Priebe et al.

It is certified that error appears in the above-identified patent and that said Letters Patent is hereby corrected as shown below:

<u>Column 37,</u>
Line 47, please delete "$NR^{11}$" and insert -- $NR^{11}_2$ -- therefor Signed and Sealed this First Day of October, 2002

Attest:

JAMES E. ROGAN
Attesting Officer    Director of the United States Patent and Trademark Office